United States Patent
Rice et al.

(10) Patent No.: US 7,581,191 B2
(45) Date of Patent: *Aug. 25, 2009

(54) GRAPHICAL USER INTERFACE FOR 3-D IN-VIVO IMAGING

(75) Inventors: Bradley W. Rice, Danville, CA (US);
Michael D. Cable, Danville, CA (US);
Binoy Mirvar, Sunnyvale, CA (US);
Olivier Coquoz, Oakland, CA (US);
Chaincy Kuo, Oakland, CA (US)

(73) Assignee: Xenogen Corporation, Alameda, CA (US)

( * ) Notice: Subject to any disclaimer, the term of this patent is extended or adjusted under 35 U.S.C. 154(b) by 781 days.

This patent is subject to a terminal disclaimer.

(21) Appl. No.: 11/006,294

(22) Filed: Dec. 6, 2004

(65) Prior Publication Data

US 2005/0149877 A1    Jul. 7, 2005

Related U.S. Application Data

(63) Continuation-in-part of application No. 10/458,579, filed on Jun. 9, 2003, now Pat. No. 7,299,420, which is a continuation of application No. 09/439,381, filed on Nov. 15, 1999, now Pat. No. 6,614,452.

(51) Int. Cl.
  G06F 3/00      (2006.01)
  G06K 9/36      (2006.01)
(52) U.S. Cl. ................. 715/764; 715/781; 715/828; 382/128; 382/280
(58) Field of Classification Search ................. 715/764, 715/781, 828; 382/128, 280
See application file for complete search history.

(56) References Cited

U.S. PATENT DOCUMENTS

| | | | |
|---|---|---|---|
| 4,948,975 A | | 8/1990 | Erwin et al. |
| 5,202,091 A | | 4/1993 | Lisenbee |
| 5,319,209 A | | 6/1994 | Miyakawa et al. |
| 5,414,258 A | | 5/1995 | Liang |
| 5,625,377 A | | 4/1997 | Jenson |
| 5,636,299 A | | 6/1997 | Bueno et al. |
| 5,637,874 A | | 6/1997 | Honzawa et al. |
| 5,650,135 A | * | 7/1997 | Contag et al. ............ 424/9.1 |

(Continued)

FOREIGN PATENT DOCUMENTS

WO    WO 94/13095    9/1994

(Continued)

OTHER PUBLICATIONS

Mahmood et al., "Near-Infrared Optical Imaging of Protease Activity for Tumor Detection", Radiology, Dec. 1999, p. 866-870.

(Continued)

*Primary Examiner*—Charles Kim
*Assistant Examiner*—Stephen R Koziol
(74) *Attorney, Agent, or Firm*—Beyer Law Group LLP

(57) ABSTRACT

The present invention provides a computer system and user interface that allows a user to readily view and analyze two-dimensional and three-dimensional in vivo images and imaging data. The user interface is well-suited for one or more of the following actions pertinent to in vivo light imaging: investigation and control of three-dimensional imaging data and reconstruction algorithms; control of topographic reconstruction algorithms; tomographic spectral imaging and analysis; and comparison of two-dimensional or three-dimensional imaging data obtained at different times.

37 Claims, 20 Drawing Sheets

U.S. PATENT DOCUMENTS

| | | | |
|---|---|---|---|
| 5,672,881 | A | 9/1997 | Striepeke et al. |
| 5,705,807 | A | 1/1998 | Throngnumchai |
| 5,738,101 | A | 4/1998 | Sappey |
| 5,740,267 | A | 4/1998 | Echerer et al. |
| 5,840,572 | A | 11/1998 | Copeland |
| 5,867,250 | A | 2/1999 | Baron |
| 5,970,164 | A * | 10/1999 | Bamberger et al. .......... 382/128 |
| 6,081,612 | A * | 6/2000 | Gutkowicz-Krusin et al. ........................ 382/128 |
| 6,217,847 | B1 * | 4/2001 | Contag et al. ................. 424/9.1 |
| 6,242,743 | B1 * | 6/2001 | DeVito et al. ........... 250/363.05 |
| 6,321,111 | B1 | 11/2001 | Perelman et al. |
| 6,332,038 | B1 | 12/2001 | Funayama et al. |
| 6,333,752 | B1 | 12/2001 | Hasegawa et al. |
| 6,364,829 | B1 | 4/2002 | Fulghum |
| 6,614,452 | B1 * | 9/2003 | Cable ........................... 715/764 |
| 6,615,063 | B1 | 9/2003 | Ntziachristos |
| 6,756,207 | B1 * | 6/2004 | Giuliano et al. ............... 435/7.2 |
| 6,775,567 | B2 | 8/2004 | Cable |
| 7,113,217 | B2 * | 9/2006 | Nilson et al. ................. 348/373 |
| 7,299,420 | B2 * | 11/2007 | Cable ........................... 715/764 |
| 2003/0193517 | A1 | 10/2003 | Cable |

FOREIGN PATENT DOCUMENTS

| | | |
|---|---|---|
| WO | WO 00/17643 | 3/2000 |
| WO | WO 00/50872 | 8/2000 |

OTHER PUBLICATIONS

Weissleder et al., "Shedding Light onto Live Molecular Targets", Nature Medicine, vol. 9, No. 1, Jan. 2003, p. 123-1218.

Collaborative Electronic Notebook Systems Association http://www.censa.org/ (Downloaded Nov. 15, 1999).

E.C. Di Mauro, et al. "Check" A generic and specific industrial inspection tool, IEE Proceedings: Vision, Image and Signal Processing, Institution of Electrical Engineers, GB, vol. 143, No. 4, Aug. 1, 1996, pp. 241-249, XP000627046, ISSN: 1350-245X.

Electronic Notebooks http://labautomation.org/la/la2000/Courses/LA2000eln.htm (discussion of electronic notebooks available prior to Nov. 15, 1999).

Hamamatsu Corporation, USA, website, http://usa.hamamatusu.com/ pp. 1-4, Apr. 27, 2001, printed on Apr. 27, 2001.

Hamamatsu, Imaging Box Instruction Manual, 55310-224-1, Nov. 2000.

Office Action dated Jan. 17, 2007 from U.S. Patent Application No. 10/458,579.

The FDA's final rule on electronic signatures and electronic records means to designers and users of automation systems—http://www.che.chaimers.se/acs-lv-97/cinf-59.html (Downloaded Nov. 15, 1999).

VetEquip Incorporated website, http://vetequip.com/1806.htm Table Top Laboratory Animal Anesthesia System, Apr. 27, 2001, printed on Apr. 27, 2001.

VetEquip Incorporated website, http://www.vetequip.com/impac.htm IMPAC$_6$ An anesthesia system designed for high volume, assembly-line type procedures, Apr. 27, 2001, printed on Apr. 27, 2001.

VetEquip incorporateed website, http://www.vetequip.com/1807.htm Mobile Laboratory Animal Anesthesia System, Apr. 27, 2001, printed on Apr. 27, 2001.

International Search Report dated Jul. 2, 2008 from PCT Application No. PCT/US05/43978.

Written Opinion dated Jul. 2, 2008 from PCT Application No. PCT/US05/43978.

* cited by examiner

US 7,581,191 B2

GRAPHICAL USER INTERFACE FOR 3-D IN-VIVO IMAGING

CROSS-REFERENCE TO RELATED APPLICATION

This application is a continuation-in-part of U.S. Patent Application entitled "GRAPHICAL USER INTERFACE FOR IN-VIVO IMAGING", filed on Jun. 9, 2003 (U.S. application Ser. No. 10/458,579) now U.S. Pat. No. 7,299,422, which is incorporated by reference herein in its entirety for all purposes and which was a continuation application of U.S. patent application Ser. No. 09/439,381, now U.S. Pat. No. 6,614,452 entitled "GRAPHICAL USER INTERFACE FOR IN-VIVO IMAGING", filed on Nov. 15, 1999, from which priority is also claimed and which is hereby incorporated by reference in its entirety for all purposes.

FIELD OF THE INVENTION

This invention relates generally to user interface software running on a computer. More particularly, the present invention relates to user interface software useful in examining and analyzing three-dimensional in-vivo images.

BACKGROUND OF THE INVENTION

In a computer application, there are numerous ways to present user information. Graphical user interfaces (GUIs) on computer systems allow easy use of windows, control icons, etc. to display information to the user. The data displayed in a window may be of different types. Some may be graphical, such as icons or pictures, or textual, such as a word processing document, or a combination of both.

When a computer interface is used for data management in a scientific application, the application may require various data-specific tools and functions. Specialized in-vivo imaging applications can present particular challenges to the design of an appropriate user interface. An in-vivo image may include a luminescent representation superimposed on a photographic representation of a specimen. The photograph provides the user with a pictorial reference of the specimen. The luminescent representation indicates internal portions of the specimen where an activity of interest may be taking place. In one example, the sample is a small animal such as a mouse and the light source could be tumor cells labeled with light emitting reporters such as firefly luciferase or fluorescent proteins or dyes. This technology is known as in vivo optical imaging.

In-vivo imaging applications are increasing in complexity and often provide copious amounts of information. Three-dimensional (3-D) imaging systems may include numerous images that correspond to a single data point or specimen. Images may include a photograph, multiple luminescent images, several structured light images from different angles, etc. Ten or more images for a single data point are common. Images taken every day for weeks or months will build a library of files and a potential overflow of information. The large number of analytical processes a researcher may perform on a data set also complicates usage. The excessive amount of data coupled with the large number of analytical processes inhibits design of an easy to manage user interface. Currently, users lack an environment that fully services user needs and permits convenient management of the large amount of data and analytical processes associated with conventional imaging.

In view of the foregoing, an improved user interface for imaging applications would be highly beneficial.

SUMMARY OF THE INVENTION

The present invention provides a computer system and user interface that allows a user to readily view and analyze two-dimensional and three-dimensional in vivo images and imaging data. The user interface is well-suited for one or more of the following actions pertinent to in vivo light imaging: investigation and control of three-dimensional imaging data and reconstruction algorithms; control of tomographic and topographic algorithms; control of spectral imaging and analysis; and comparison of two-dimensional or three-dimensional imaging data obtained at different times.

In accordance with one embodiment of the present invention, a computer system is provided with an image measurement window, which allows the user to perform certain operations that are particularly useful for constructing, presenting and analyzing a tomographic representation. In addition to having conventional computer hardware such as a processor, memory, and a display, the computer system includes a graphical user interface having one or more windows that provide images and one or more tools that facilitate topographic and tomographic reconstruction. By providing a large number of features in a single easy-to-use graphical user interface, interfaces of this invention permit users to manage and wield a large amount of data flexibly and comfortably.

In one aspect, the present invention relates to a computer system capable of displaying and analyzing an image. The computer system comprises one or more processors and one or more user input devices. The computer system also comprises a display capable of displaying the image and associated information in particular ways responsive to input signals from one or more of the input devices and signals from one or more of the processors. The image comprises a three-dimensional representation of an object surface superimposed with a three-dimensional light emitting representation, which includes information describing a location and magnitude of electro-magnetic radiation located within the object. The computer system further comprises a graphical user interface running on one or more of the processors and providing one or more reconstruction tools. When a user uses one of the reconstruction tools, the computer system reconstructs the three-dimensional light emitting representation of the electromagnetic radiation located within the object.

In another aspect, the present invention relates to a computer system capable of displaying and analyzing an image. The computer system also comprises a display capable of displaying the image. The image comprises a three-dimensional topographic representation of an object surface superimposed with a light emitting representation, which includes information describing a location and magnitude of light emitted from a surface of the topographic representation. The computer system further comprises a graphical user interface running on one or more of the processors and providing one or more topographic representation tools. When a user selects the one or more topographic representation tools, the computer system constructs the topographic representation of the object.

In yet another aspect, the present invention relates to a computer system capable of displaying and analyzing an image. The computer system also comprises a display capable of displaying the image. The image comprises a three-dimensional representation of an object surface superimposed with a three-dimensional light representation of the object, which includes information describing a location and magnitude of a light source located within the object. The computer system further comprises a graphical user interface running on one or more of the processors and providing one or more spectral analysis tools. When a user inputs spectral information using one of the spectral analysis tools, the computer system performs a reconstruction of the light source according to input provided with the one or more spectral analysis tools.

In yet another aspect, the present invention relates to a computer system capable of displaying and analyzing an image. The computer system comprises one or more processors and one or more user input devices. The computer system also comprises a display capable of displaying the image and associated information in particular ways responsive to input signals from one or more of the input devices and signals from one or more of the processors. The image comprises a) a first light emitting representation of the object, the first light emitting representation including first information describing a location and magnitude of light emitted from within the object, and b) a second light emitting representation of the object, the second light emitting representation including second information describing the location and magnitude of light emitted from within the object. The computer system further comprises a graphical user interface running on one or more of the processors and providing one or more evaluation tools, wherein when a user uses one of the reconstruction tools, the computer system quantitatively evaluates the first information and the second information.

These and other features and advantages of the invention will be described in more detail below with reference to the associated figures.

BRIEF DESCRIPTION OF THE DRAWINGS

The present invention is illustrated by way of example, and not by way of limitation, in the figures of the accompanying drawings and in which like reference numerals refer to similar elements and in which.

DESCRIPTION OF THE PREFERRED EMBODIMENTS

Figure 1A:
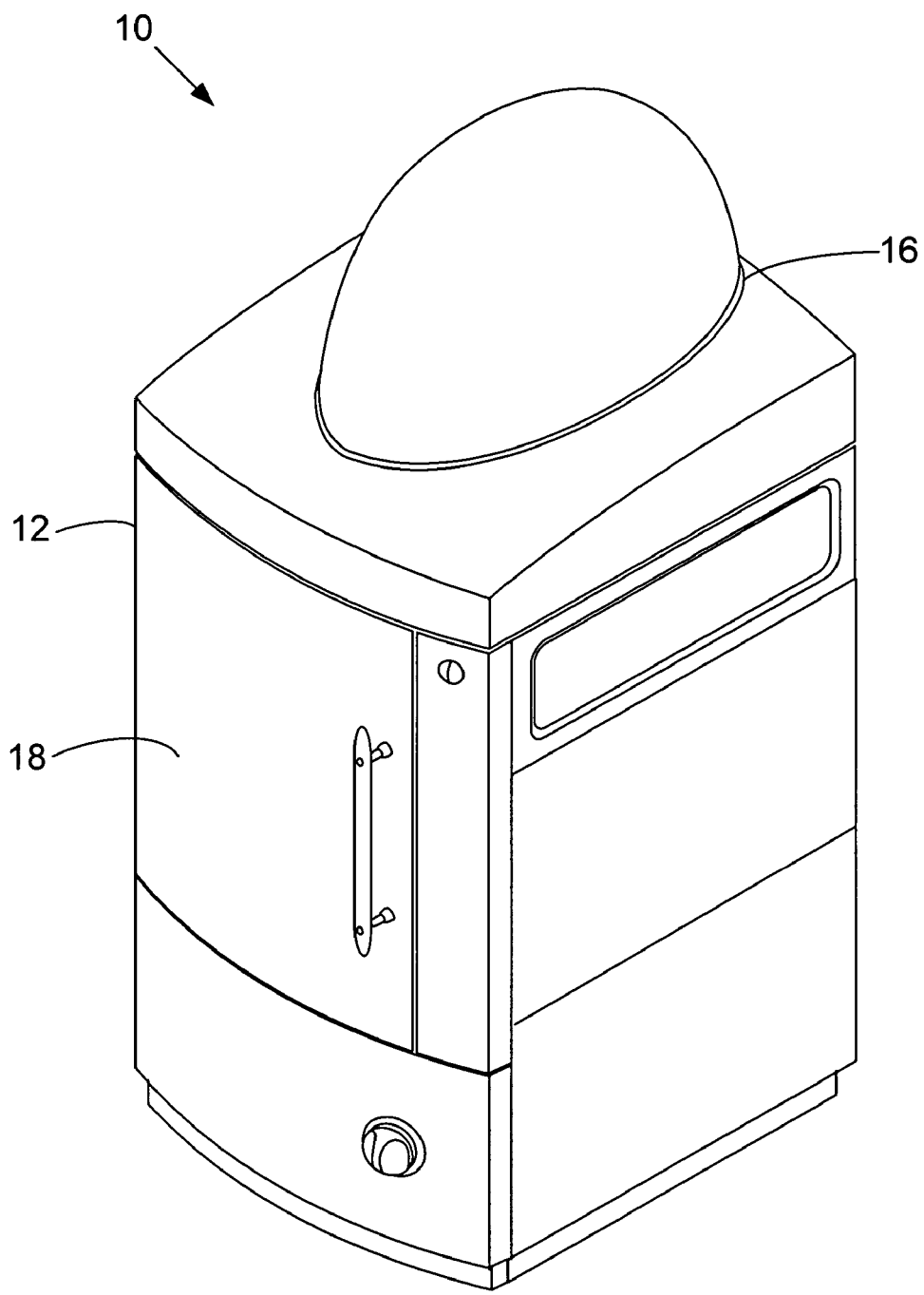
FIGS. 1A and 1B illustrate a perspective-view of an imaging system in accordance with one embodiment of the present invention.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

A graphical user interface (GUI) is provided which allows a user to perform numerous operations suitable for image analysis for an in-vivo imaging application. Using a GUI of this invention, the user may create and manipulate analysis tools and perform a wide variety of measurements on complex images (such as three-dimensional reconstructed in-vivo images of an internal light source) conveniently and efficiently. In addition, the present invention allows a user to manipulate and flexibly present images and image data, manipulate tomographic reconstruction parameters, perform structured light and topographic reconstructions, and numerous additional tasks relevant to an in-vivo imaging application.

The present invention provides both topographic and tomographic imaging tools. Topographic imaging refers to the surface characterization of an object. In one embodiment, the present invention uses structured light to determine surface topography for an object. Tomographic imaging refers to information inside the surface. This is useful for localizing internal objects in 3-D inside an object. An exemplary illustration of these two imaging forms uses a 2-D planar slice through an object: topography gives the surface (the outer bounding line), while tomography gives everything inside the bounding surface.

One embodiment of this invention pertains to graphical user interfaces for presenting and analyzing an "emissions" image—or luminescence image—that includes light data corresponding to an electro-magnetic radiation source internal an object. Although the present invention will now primarily be described with respect to light imaging, it is understood that other forms of electromagnetic radiation may also be included herein such as infrared, near IR, ultraviolet, and the like. In one application, the object is a biological specimen such as a mouse. The luminescence image comprising light is taken without using light sources other than those emitted from the specimen itself. Luminescence from the object is recorded as a function of position to produce a two-dimensional luminescence image. A computer system that operates a graphical user interface described herein may convert two-dimensional light images produced by a camera into three-dimensional luminescence images and data. One approach to generating such two-dimensional luminescence images is described in U.S. Pat. No. 5,650,135 issued to Contag et al. on Jul. 22, 1997. The entire disclosure of that patent is incorporated herein by reference. Constructing three-dimensional information from two-dimensional images is described in further detail below.

Figure 1B:
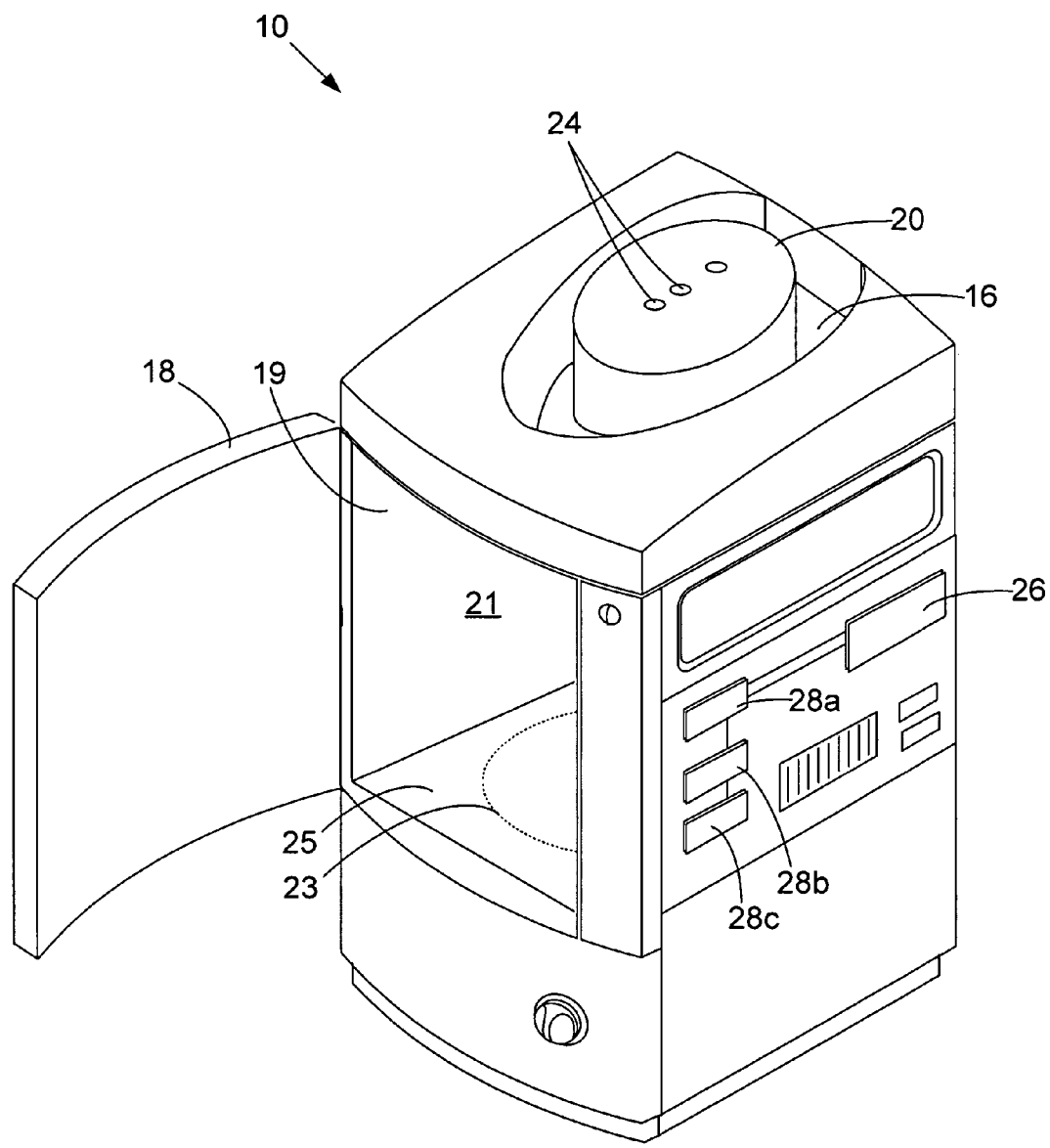

FIGS. 1A and 1B illustrate an imaging system 10 configured to capture photographic, luminescence, structured light and fluorescent images. Imaging system 10 comprises an imaging box 12 having a door 18 and inner walls 19 (FIG. 1B) that define an interior cavity 21 that is adapted to receive a light-emitting sample or test device in which low intensity light is to be detected. Imaging box 12 is suitable for imaging including the capture of low intensity light on the order of individual photons, for example. Imaging box 12 is often referred to as "light-tight". That is, box 12 seals out essentially all of the external light from the ambient room from entering the box 12, and may include one or more seals that prevent light passage into the box when door 18 is closed.

Imaging box 12 includes an upper housing 16 adapted to receive a camera 20 (FIG. 1B). A high sensitivity camera 20, e.g., an intensified or a charge-coupled device (CCD) camera, is mounted on top of upper housing 16 and positioned above imaging box 12. CCD camera 20 is capable of capturing luminescent, fluorescent, structured light and photographic (i.e., reflection based images) images of a living sample or test device placed within imaging box 12. CCD camera 20 is cooled by a suitable source such as a refrigeration device that cycles a cryogenic fluid to cool the CCD camera via conduits that communicate the cooling fluid into channels 24.

Imaging system 10 may also comprise a lens (not shown) that collects light from the specimen or test device and provides the light to the camera 20. A stage 25 forms the bottom floor of imaging chamber 21 and includes motors and controls that allow stage 25 to move up and down to vary the field of view 23 for camera 20. In one embodiment, the motors and controls permit movement of stage 25 in 2 degrees-of-freedom relative to a camera mounted on the side of imaging box 12. A multiple position filter wheel may also be provided to enable spectral imaging capability. Imaging box 10 may also include one or more light emitting diodes on the top portion of chamber 21 to illuminate a sample during photographic image capture. Other features may include a gas anesthesia system and heated stage to maintain an animal's body temperature during image capture and anesthesia.

One suitable imaging system is the IVIS-200 as provided by Xenogen corporation from Alameda, Calif. Further description of various elements included in the IVIS-200 are provided in commonly owned U.S. Pat. No. 6,775,567 entitled "Improved Imaging Apparatus", which is incorporated by reference herein in its entirety for all purposes. One suitable 3-D system is provided in commonly owned pending patent application Ser. No. 09/905,668 entitled "3-D Imaging Apparatus for In-Vivo Representations", which is incorporated by reference herein in its entirety for all purposes. Although imaging system 10 is shown with a single cabinet design, other embodiments of the present invention include a disparate imaging box 12 and computer system, such as a commercially available computer system purchased separately from imaging system 10, that includes processing system 28 and a dedicated display such as an LCD or CRT monitor.

FIG. 1B shows system 10 with the removal of a side panel for imaging box 12 to illustrate various electronics and processing components included in system 10. Imaging system 10 comprises image processing unit 26 and processing system 28. Image processing unit 26 optionally interfaces between camera 20 and processing system 28 and may assist with image data collection and video data processing.

Processing system 28, which may be of any suitable type and included in a separate computer, comprises hardware including a processor 28a and one or more memory components such as random-access memory (RAM) 28b and read-only memory (ROM) 28c. Processor 28a (also referred to as a central processing unit, or CPU) couples to storage devices including memory 28b and 28c. A fixed disk is also coupled to processor 28a and provides data storage capacity. The fixed disk may be used to store graphical user interface software, control software, other imaging programs, imaging data and the like.

Processor 28a communicates with various components in imaging box 12. To provide communication with, and control of, one or more system 10 components, processing system 28 employs software stored in memory 28c that is configured to permit communication with and/or control of components in imaging box 12. Processing system 28 may also interface with a visual display such as a computer monitor and input devices such as a keyboard and mouse. A graphical user interface (as described below) that facilitates user interaction with imaging system 10 may also be stored on system 28, output on a visual display and receive user input from a keyboard, mouse or other computer input. The graphical user interface allows a user to view imaging results, acts an interface to control the imaging system 10, and provides various image analysis tools and resources as described below.

Processing system 28 may comprise software, hardware or a combination thereof. System 28 may also include additional imaging hardware and software, graphical user interface software, image processing logic and instructions for processing information useful to an in-vivo imaging application and provided by a graphical user interface. While imaging system 10 includes processing system 28 included therein, some embodiments of the invention employ an external processing system that couples to imaging system 10. In this case, a graphical user interface as described herein is stored as computer implement instructions on a separate disk or computer readable media, such as a CD provided with an imaging system. This permits any computer to then run a graphical user interface as described herein and interface with imaging system 10. In another embodiment, the graphical user interface as described herein is provided on a separate disk or computer readable media such as a CD apart from any imaging system. This permits any computer, whether associated with an imaging system or not, to run a graphical user interface as described herein and analyze in-vivo images—regardless of whether the user has access to an imaging system such as system 10. In this case, the user need only acquire any imaging data and images to be analyzed.

Figure 2:
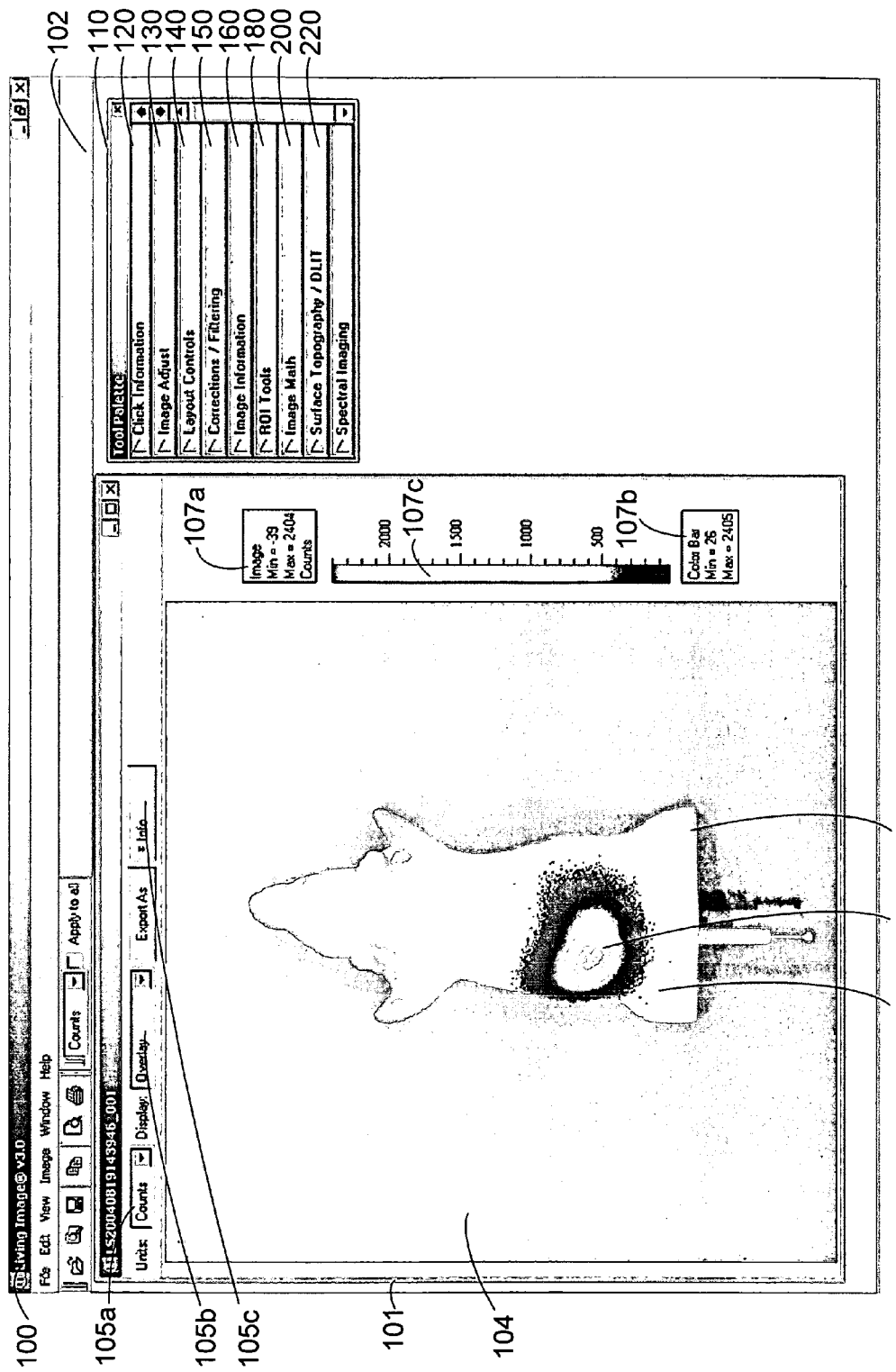
FIG. 2 illustrates a graphical user interface (GUI) in accordance with one embodiment of the present invention.

FIG. 2 illustrates a graphical user interface (GUI) 100 in accordance with one embodiment of the present invention. GUI 100 comprises an image window 101 and a tool palette 102 originally contained in a GUI window 103.

GUI window 103 corresponds to an in-vivo user interface program stored and run on a computer. Upon initiation, GUI window 103 includes both image window 101 and tool palette 102. GUI window 103 may also include regular graphical user interface tools, such as file opening, print and file saving buttons. One suitable example of an in-vivo user interface program is Living Image 3D Analysis Package 1.0 as provided by Xenogen Corporation of Alameda, Calif.

Image window 101 includes an image 104 and image window tools 105a-d. As shown, image 104 comprises an overlay image that includes a visual superposition of a photographic image 106 and a luminescence image 108. In this example, the photographic image 106 comprises a plastic model of a mouse 109 including a body material that optically resembles mammalian tissue. Photographic representation 106 provides a user with a visual frame of reference for one or more objects 109.

Luminescence image 108 comprises a light representation of a light source internal to object 109. As will be discussed below, luminescence image 108 may comprise two-dimensional or three-dimensional light data. Luminescence image 108 may thus include light data on the surface of object 109 and/or light data internal to the surface and within the volume of object 109. In many cases, image 108 includes photon emission data derived over time using an imaging system such as that described above. In one embodiment, a 2-D luminescence image 108 indicates the number of times each detector pixel in a camera has received a photon over a defined length of time. In other words, the luminescence representation may display magnitude values representing the photon counts at the individual detector pixels. Regions of the object emitting radiation (e.g., photons) will appear in the luminescence representation.

A luminescence image may include a light representation of a light source internal to the object that indicates the presence of a biocompatible entity, for example. The entity can be a molecule, macromoloecule, cell, microorganism, a particle or the like. Thus, an in-vivo analysis may include detecting localization of a biocompatible entity in a mammalian subject. Alternatively, luminescent images taken on a daily basis for a month may be used to track the biocompatible entity over time, such as the progression of a cancer in a mouse.

Data in the luminescence representation typically has one or more distinct luminescent portions of interest. Although the image window 101 displays an overlay image comprised of two separate images, most analysis is performed on the luminescence image 108. In particular, an analysis may include a summation of the illumination magnitudes over the pixels within a portion of the luminescence representation. 3-D luminescence images are derived using tomographic reconstruction algorithms described in further detail below.

Window tools 105a-d permit a user to alter display of one or more images in window 101. Units tool 105a permits a user to select counts or photons as the units for luminescent image 108. Digital cameras output raw image data in "analog-to-digital convertor units" (ADU) or "counts". Counts are uncalibrated units that refer to the amplitude of the signal detected by the digitizer incorporated into the CCD camera. The number of counts detected by the digitizer is proportional to the number of photons incident on a given CCD pixel. A distinction between absolute physical units and relative units of "counts" is that the radiance units refer to light emission from the animal or phantom device itself; as opposed to counts which refers to light emission incident on the detector. The use of real physical units (radiance) in a diffuse tomographic reconstruction allows the source intensity to be reconstructed in real physical units of flux or photons/sec.

Display tool 105b permits a user to select from any images for the current file. Exemplary images for the current data set are shown in FIG. 3B and include an overlay image, photographic image, luminescent image, background image, saturation map, structured light image, a reference, and 3-D view. When selected, Info button tool 105c illustrates information related to image capture of the image shown in window 11.

Window 101 also includes a luminescence image display section 107 to assist in viewing and comprehension of luminescent image 108. The luminescent image display section 107 includes a maximum and minimum luminescence 107a. The image maximum indicates the magnitude of the highest data value (photons or camera counts) for any pixel in luminescent image 108. A legend maximum and legend minimum 107b are also provided. The legend maximum indicates the maximum data value (photon count) for window 301. A scale 107c provides a visual mapping between a range of colors for information in luminescent image 108 and a magnitude range. Individual luminescence magnitudes correspond to shades of gray or a color indicated by scale 107c.

Tool palette 102 includes a plurality of user interface control components for facilitating manipulation and analysis of information in the image window 101. As shown, tool palette 102 includes a separate window that may be moved independently of image window 101. For example, a user may click on a border region of tool palette 102 and drag it outside of living image window 103, thereby unimpeding view of any information in window 101.

Tool palette 102 provides a centralized resource that organizes numerous data manipulation and analysis tools for in vivo imaging. In one embodiment, tool palette 102 groups control tools into thematic toggles. A toggle refers to a graphical tool that permits simplified expansion and contraction of tool sections and information related to a particular subject. Common conventional toggles include pulldown menus, buttons, click boxes, etc. While tool palette 102 illustrates similar toggles when no individual toggle has been activated, it is understood that tool palette 102 may include different toggle types as desired by design. Selecting any of the toggles in tool palette 102 opens up a tool section corresponding to each toggle (see FIGS. 3A-3I). As illustrated, the tool palette 102 includes a click information toggle 110, image adjust toggle 120, layout controls toggle 130, corrections and filtering toggle 140, image information toggle 150, ROI tools toggle 160, image math toggle 180, surface topography and DLIT toggle 200, and spectral imaging toggle 220. Other arrangements are contemplated. Since each section may include a large number of individual tools, providing the ability to toggle and minimize the size of individual sections reduces the size of tool palette 102 and simplifies use for GUI 100.

Figure 3A:
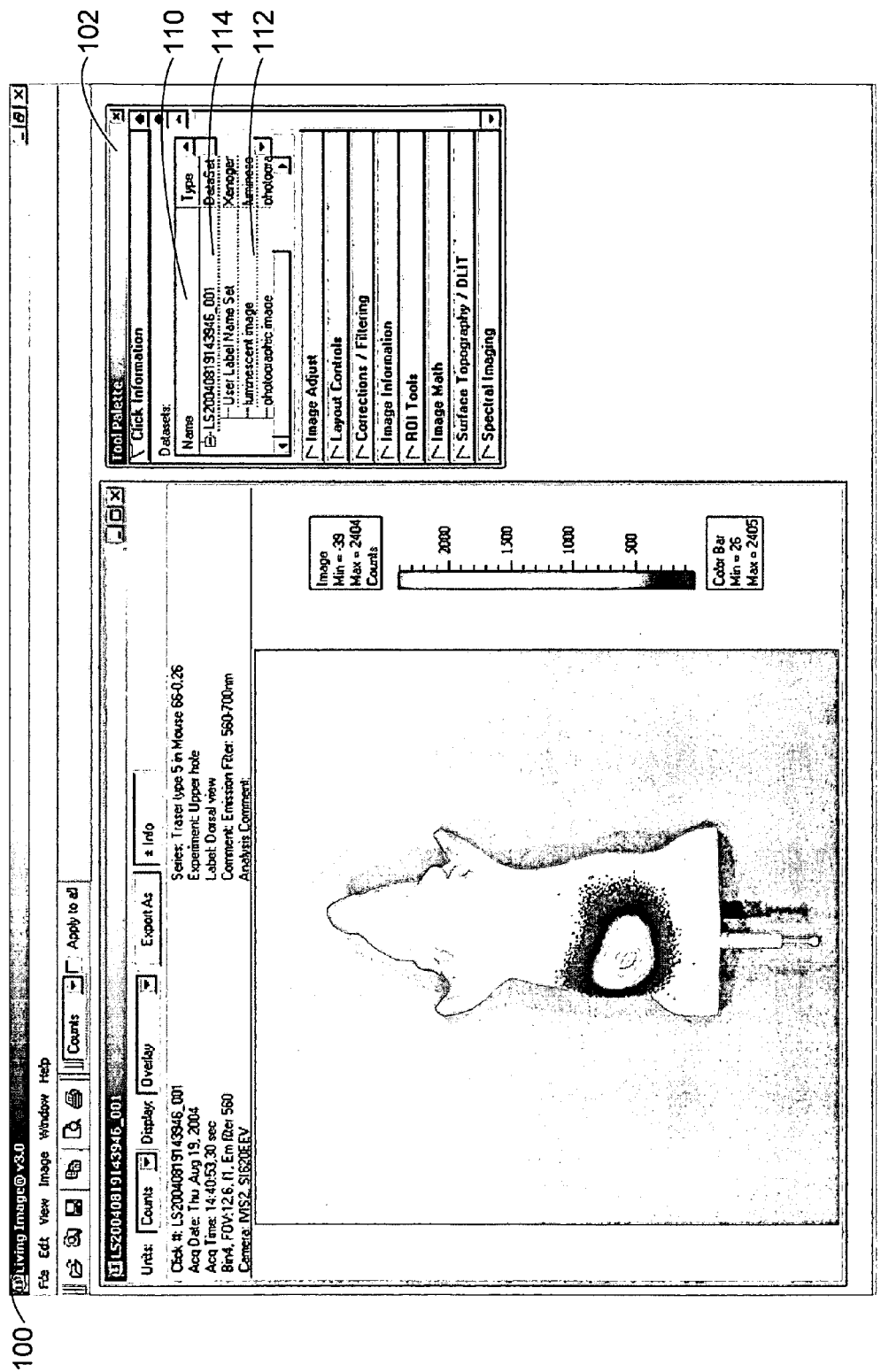
FIG. 3A illustrates an imaging GUI with a click information toggle enabled and showing a click information section.
Figure 3B:
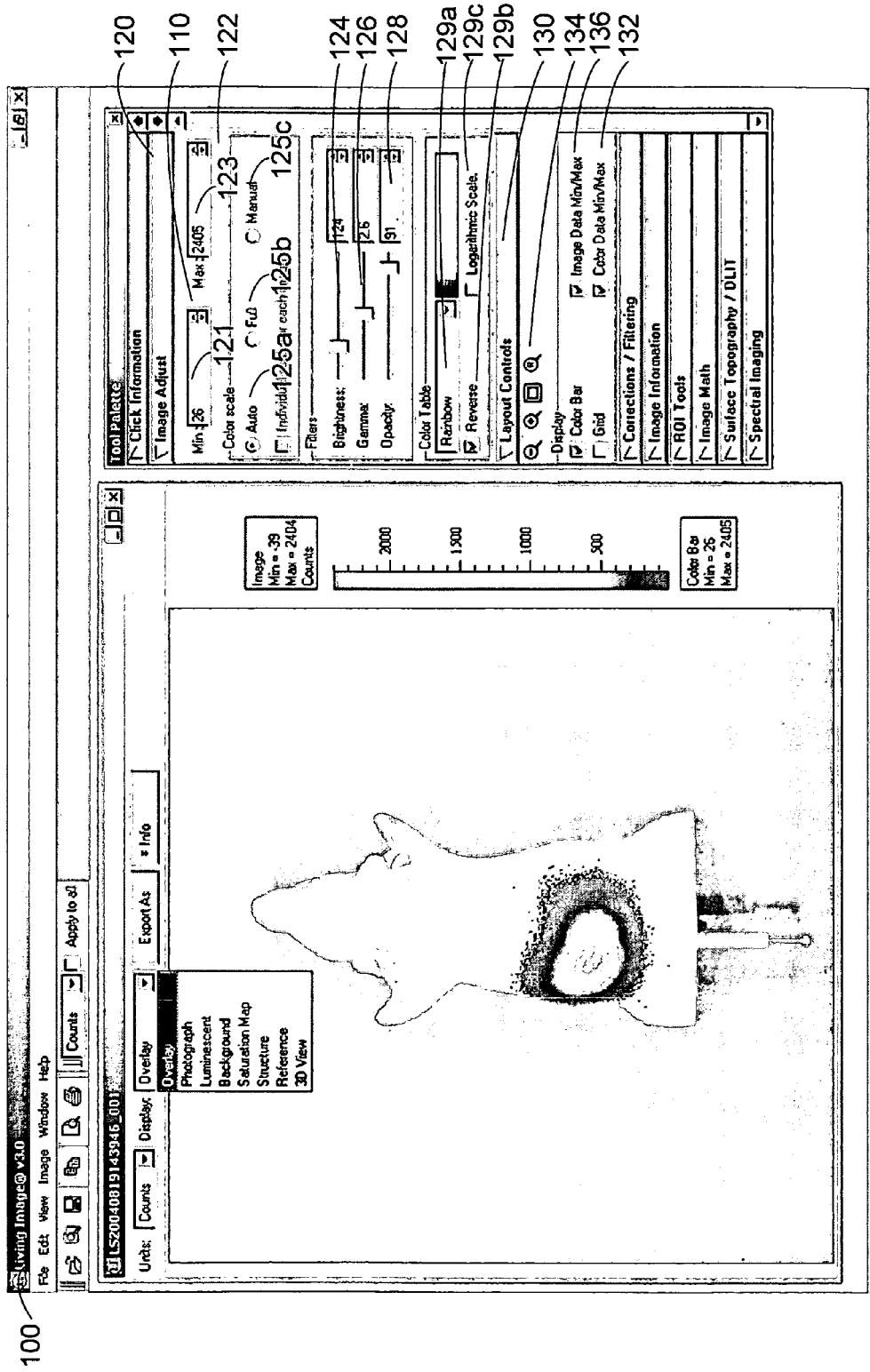
FIG. 3B illustrates an imaging GUI with both the image adjust toggle and layout controls toggle enabled and showing both an image adjust section and a layout controls section.

FIG. 3A illustrates GUI 100 with click information toggle 110 enabled and showing click information section 112. Click information section 112 identifies information for the data set currently being displayed. A click number 114 uniquely identifies the current data set being displayed. Information presented in section 112 may include data related to object 109, a specific date and time for image capture, the camera used, any information relevant to a particular image (camera settings, camera type, stage position, or the use of any filters during image capture, other photographic image capture info, other luminescence image capture info, other structured light info, etc.).

FIG. 3B illustrates GUI 100 with both the image adjust toggle 120 and layout controls toggle 130 enabled and showing both an image adjust section 122 and a layout controls section 132.

Image adjust section 122 includes tools that allow a user to manipulate the presentation of photographic image 106 and luminescence image 108. To manipulate the presentation of the photographic image 106, the display function section 314 includes a brightness setting 124 and gamma setting 126. Brightness setting 124 allows a user to improve visual perception of photographic image 106 by allowing brightness adjustment for image 106. Gamma setting 126 allows a user to set the sharpness for image 106.

To manipulate presentation of luminescence image 108, image adjust section 122 includes opacity setting 128, minimum luminescence 121, maximum luminance 123, color scale 125 and color table 127.

Opacity setting 128 allows a user to vary the brightness of luminescent image 108 relative to photographic image 106. Thus, increasing opacity setting 128 creates more visible luminescent data on the photographic image 106. Decreasing opacity setting 128 increases transparency in the luminescent data (and visibility of the underlying photographic data in this overlay area).

Maximum luminance 123 allows a user to designate the maximum data value displayed in luminescent image 108. Any pixels within the luminescence representation having a data value (e.g., a photon count) at or over this maximum will be displayed with a color corresponding to the maximum luminance 123. Minimum luminescence 121 allows a user to designate the minimum data value displayed in luminescent image 108. Any data within luminescent image 108 having a data value below the minimum are not displayed. Maximum luminance 123 and minimum luminescence 121 may be useful when a user wants to selectively clear an overlay image of outlying data for a particular analysis. Minimum luminescence 121 is also useful when a user wants to clear noise from image 108.

Full setting 125b provides a default option for the presentation of the luminescence image 108 and sets maximum luminance 123 and minimum luminescence 121 to the 'full range' of values in the luminescence image 108. Auto tool 125a sets maximum luminance 123 and minimum luminescence 121 to a predetermined set of values for image 108. For example, a predetermined range may set maximum luminance 123 at 95% of the maximum photon count for image 108 and minimum luminescence 121 at 5% of the maximum photon count. Manual setting 125c permits a user to input maximum luminance 123 and minimum luminescence 121.

Color table 129a allows a user to change the color scheme used in scale 107c. A gray scale or suitable color scheme (rainbow, yellow hot, blue hot, planet Earth, etc.) then indicates magnitude in luminescent image 108. Reverse toggle 129b reverses the color order for indicating magnitude. Logarithmic scale toggle 129c changes the luminescent data color bar scale to be logarithmic instead of linear in image 108.

Layout controls section 132 includes tools that allow a user to alter display of in window 101. Zoom tools 124 include a zoom in, zoom out, rectangle zoom and refresh zoom. Toggle boxes 136 allow a user to apply or remove individual elements of luminescence image display section 107.

Figure 3C:
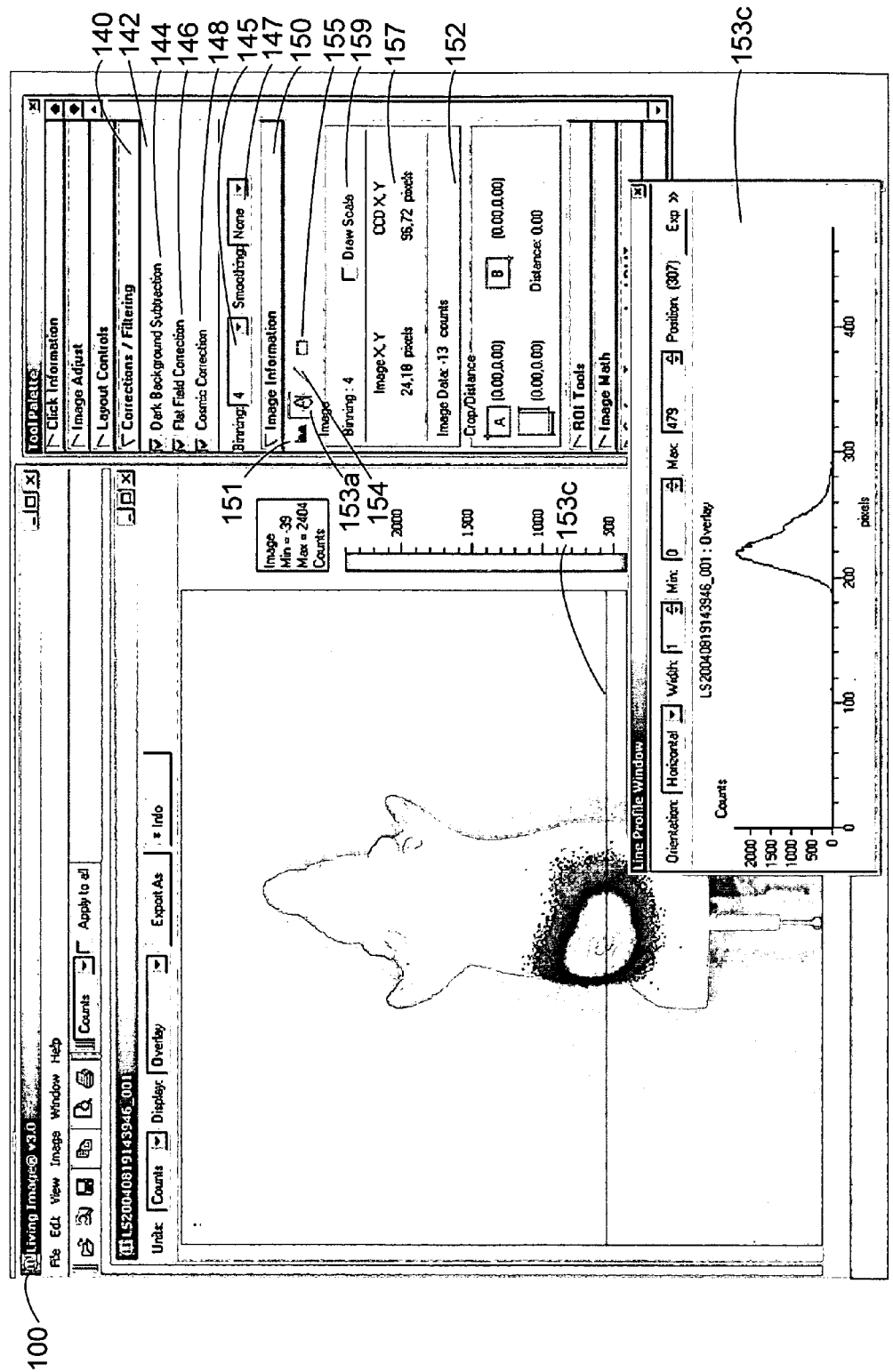
FIG. 3C illustrates an imaging GUI with both the corrections and filtering toggle and image information toggle enabled and showing both a corrections and filtering section and an image information section.

FIG. 3C illustrates GUI 100 with both the corrections and filtering toggle 140 and image information toggle 150 enabled and showing both a corrections and filtering section 142 and an image information section 152.

The image for a blank view of the imaging chamber without an object 109 is often referred to as a 'dark image'. Often, it is desirable to calibrate a photographic image and luminescence image to compensate for the blank view. The dark image may characterize offsets and leakage current in a camera, for example, which should be subtracted from images taken with the camera. To allow dark image correction, the display function section 314 includes a dark background subtraction checkbox tool 144.

Corrections and filtering section 142 also includes a flat field correction checkbox tool 146, which when toggled, corrects for any known variations in a camera lens illumination field in window 101. Some images may contain bright spots corresponding to radiation anomalies during extended image capture. To allow correction for such defective pixels, section 142 also includes a cosmic correction checkbox tool 144. Corrections and filtering section 142 also includes binning tool 145 and smoothing tool 147 that allow a user to alter and manipulate the pixelated display of luminescent data. For example, binning may account for insufficient information per pixel. When a user applies a 4× binning, GUI 100 halves the number of pixels in each direction for the luminescence image 108 to produce a new pixel array comprising the magnitude of four previous pixels in a single new pixel (to alter statistical analysis).

Image information section 152 includes various tools that permit a user to obtain luminescence and statistical data within luminescent image 108. Selecting histogram button 151 produces a histogram for luminescent image 108 (a graph of luminescent wavelength versus the range of wavelengths in the luminescent image 108).

Line profile tool 153a allows a user to draw a line 153b across a portion of luminescent image 108 and read luminescent data along the line. The user may also click on line 153b and move the line to a desired portion of luminescent image 108. Selecting line profile tool 153a also opens a line profile window 153c. Line profile window 153c comprises a chart of photon (or counts depending on which is currently selected) vs. position for line 153b.

Distance measurement tool 154 allows a user to determine the straight-line distance between two points on an image in window one a line. Coordinate display 157 outputs the position of a pointer used within image window 101. Draw scale tool 159, when selected or applied, applies a ruler to orthogonal sides of image window 101 within GUI 100. Image crop tool 155 allows a user to select a subspace for the image 104. Crop dimension and distance information is also provided in a bottom portion of image information section 152

FIG. 3C also illustrates a non-maximum size for the GUI 100 window. In this case, tool palette 102 is not restricted to use within GUI 100 window and may be moved outside the window to a more convenient location as desired by a user. In addition, line profile window 153c is also created outside of the main border for GUI 100. Creating independent windows for window 101, tool palette 102 and subsequent windows open shearing usage of GUI 100 such as line profile window 153c gives a user the flexibility to customize layout and visibility of numerous windows as desired.

Figure 3D:
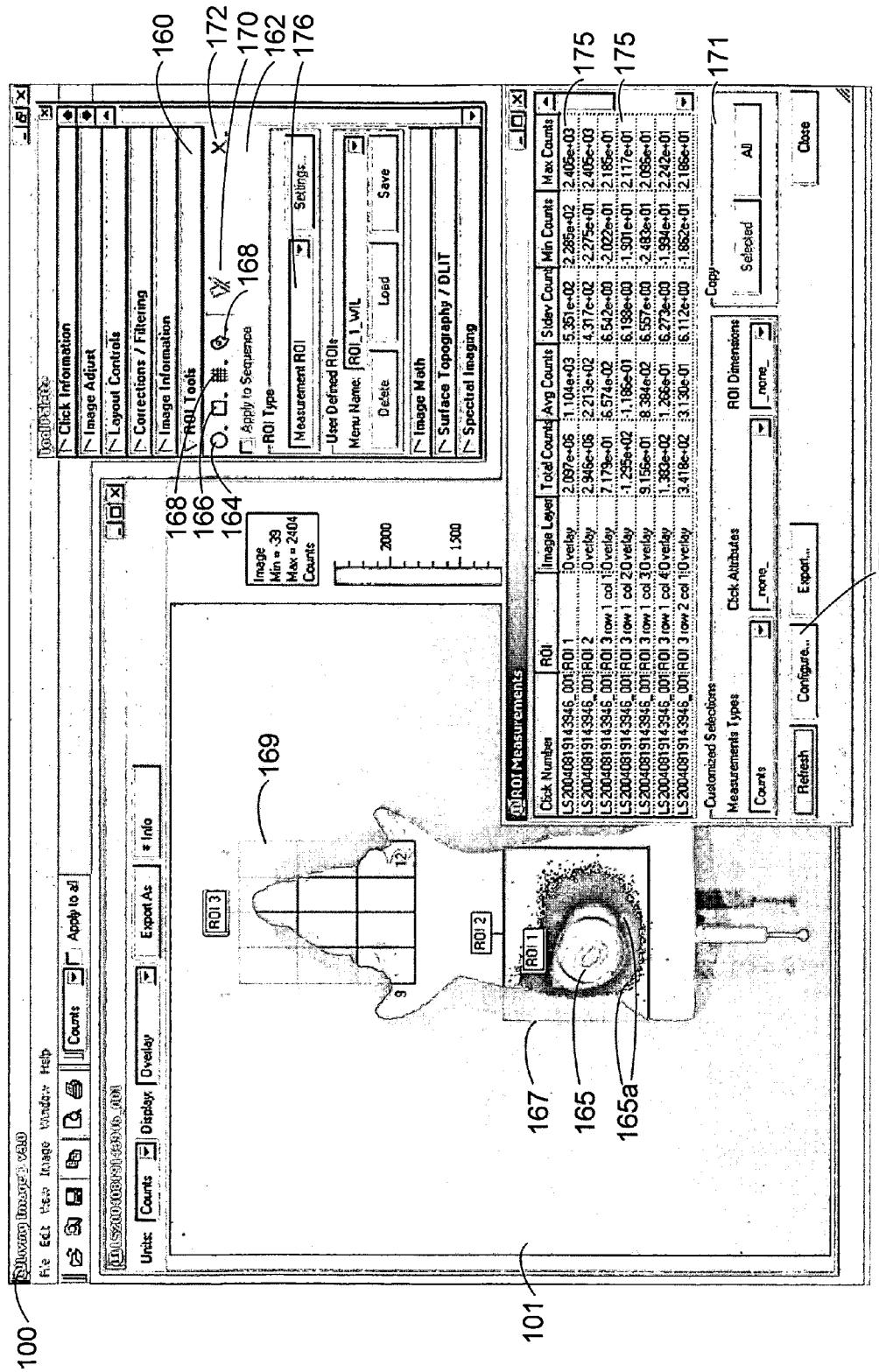
FIG. 3D illustrates an imaging GUI with a region of interest (ROI) tools toggle enabled and showing an ROI tools section in accordance with a specific embodiment of the present invention.

FIG. 3D illustrates GUI 100 with the ROI tools toggle 160 enabled and showing ROI tools section 162 in accordance with a specific embodiment of the present invention.

ROI section 162 includes controls for allowing a user to create and manipulate tools which enable simple and flexible analysis of tomographic data within the image measurement window 101. Create circle button 164 allows a user to create a circular or elliptical region of interest (ROI) 165 with one action on tool palette 102. For example, the user simply clicks on button 164 with a pointer and a new circular 165 (ROI 1) appears in window 101. In one embodiment, great circle button 164 includes a pulldown menu that allows the user to create multiple circles (e.g., 2, 3, 4) at a time. Create rectangle button 166 allows a user to create a square or rectangular region of interest 167 (ROI 2). A grid button 168 allows user to create a grid ROI 169. A pulldown menu for grid button 168 allows a user to set the number of rows and columns in grid 169 (e.g., 2×3, 3×4, 5×8, etc). Upon creating an ROI, a label is attached to the geometric outline of the ROI for user clarity. A remove tool 172 allows a user to delete an ROI in window 101. ROI section 162 includes a storage section 176 that permits ROIs to be saved and labeled. In addition, storage section 176 allows a user to load and re-access previously stored ROIs.

GUI 100 also allows a user to manipulate each ROI. The ROI currently being viewed is indicated to the user via highlights. Thus, after the circle 165 is created, the size, shape, position and orientation of the circle 165 may be altered. In one embodiment, clicking a pointer on circle 165 reshapes the ROI. Alternatively, clicking a pointer on a highlight 165a and dragging may reshape the ROI. Similarly, a user may change dimensions for ROI 2 or ROI 3 within window 101 by clicking on a corner feature of the ROI and dragging a side.

ROI section 162 includes GUI controls that allow a user to measure and analyze tomographic data within window 101. Activating measure button 170 creates ROI measurements window 171, which includes an entry 175 for each ROI currently displayed in window 101. In addition, each section of grid ROI 169 includes a separate entry 175. As shown, each entry 175 includes a click number field in that designates the current image 108 being analyzed, and ROI designation field, an image layer field, a field for the total number of counts in an ROI, a field for an average number of counts in an ROI, and fields that correspond to other statistical measures for luminescence data in the ROI. The fields (and corresponding data displayed) for each entry 175 may vary with design.

Figure 3E:
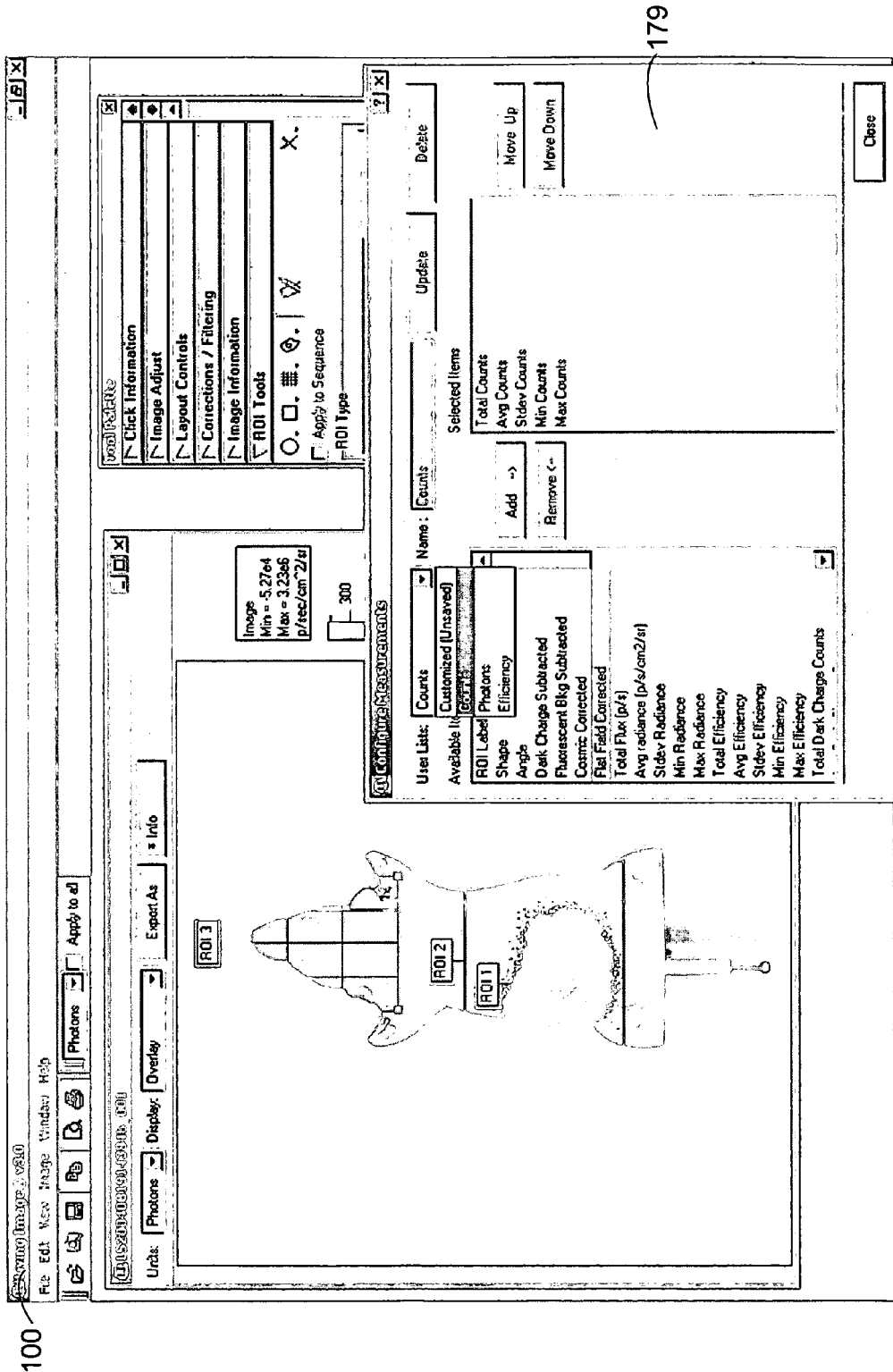
FIG. 3E illustrates an imaging GUI with an exemplary configure measurements window in accordance with a specific embodiment of the present invention.

A configure button 177 allows a user to specify which fields are displayed in ROI measurements window 171. In a specific embodiment, configure button 177 brings up a separate configure measurements window 179 that permits control of fields displayed in ROI measurements window 171. As shown in FIG. 3E, configure measurements window 179 includes a variety of tools that enable a user to tailor what information is presented for a region of interest. For example, available fields are listed and an add button allows a user to add any field to ROI measurements window 171. In general, any information relating to an image shown in window 101 may include a separate designated field. Exemplary fields include average radiance, minimum and maximum radiance, total efficiency, total or average fluorescent background counts, ROI pixel statistics, area, linear or volume dimensions, sequence identification, date and time, binning, exposure, field of view, f-stop, image angle, fluorescence level, experiment, analysis comments, etc.

Although GUI 100 has so far been discussed primarily in the context of manipulating a single two-dimensional luminescent and photographic overlay image, the analysis tools and methods of the present invention are also well-suited for use with three-dimensional and other advanced applications.

Figure 4A:
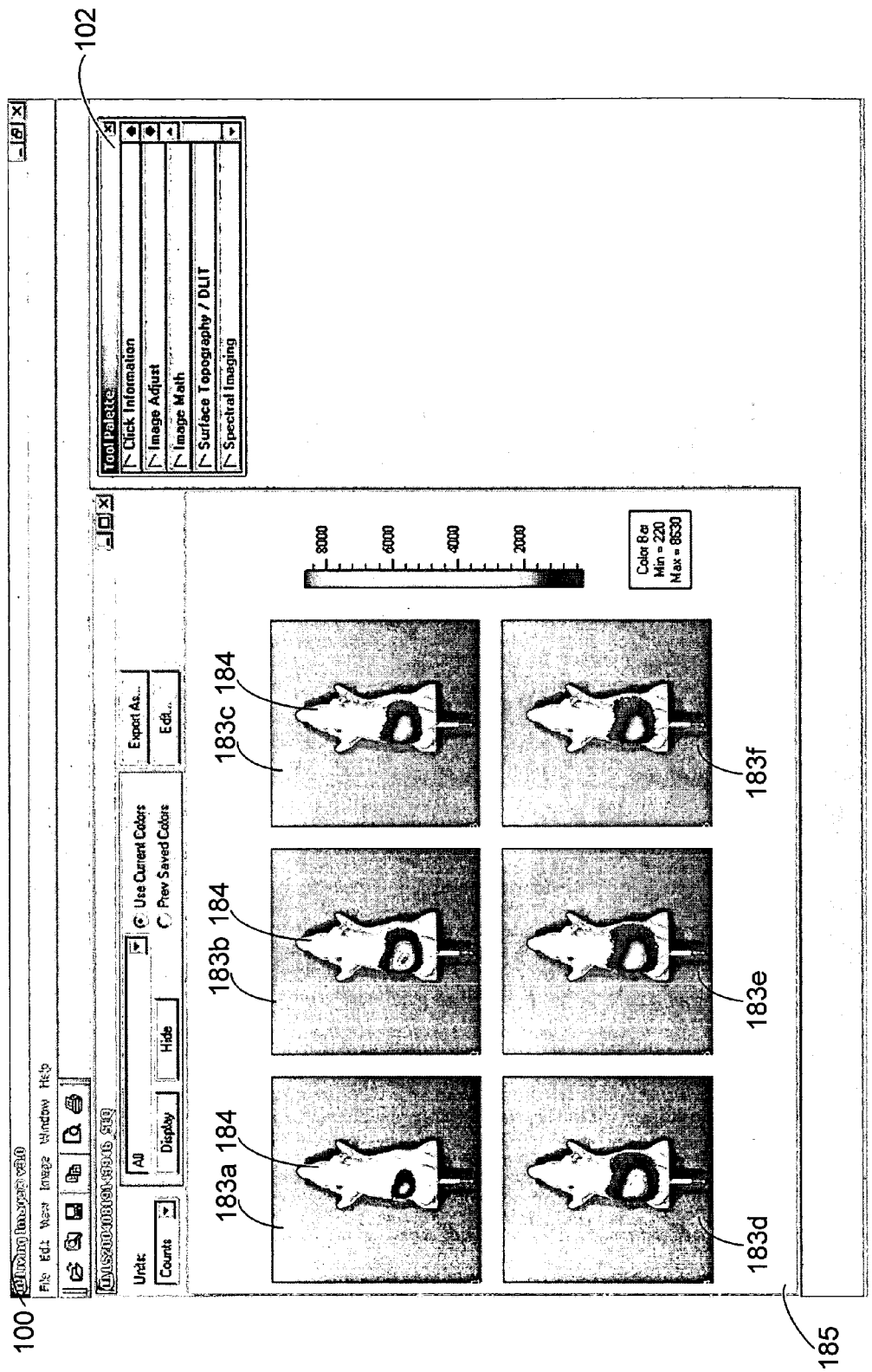
FIG. 4A illustrates an imaging GUI with a sequence window in accordance with one embodiment of the present invention.

FIG. 4A illustrates a sequence window 185 in accordance with another embodiment of the present invention. Sequence window 185 permits a user to conveniently view and evaluate multiple images for a particular mammal 184. This is useful in analyzing images where multiple wavelengths or multiple viewing angles have been taken of an object. Alternatively, each overlay image 183a-f may correspond to luminescent imaging performed on the same mammal 184 on six consecutive days and sequence window 185 shows progression of an internal light source over time.

Sequence window 185 allows a user to evaluate the progress of light-emitting cells in a small laboratory animal such as a mouse or rat. This finds use in a wide range of applications in pharmaceutical and toxilogical research, such as in vivo monitoring of infectious diseases, tumor growth in metastases, transgene expression, etc. The ability to detect signals in real-time and in living animals means that the progression of a disease or biological process can be readily studied throughout an experiment with the same mammal 184.

A user may double-click or select any of the overlay images 183 and perform measurements and/or adjustments to each image 183 with any of the tools described above. In addition, GUI 100 also provides tools for comparing one overlay image 183 with another overlay image 183.

Figure 4B:
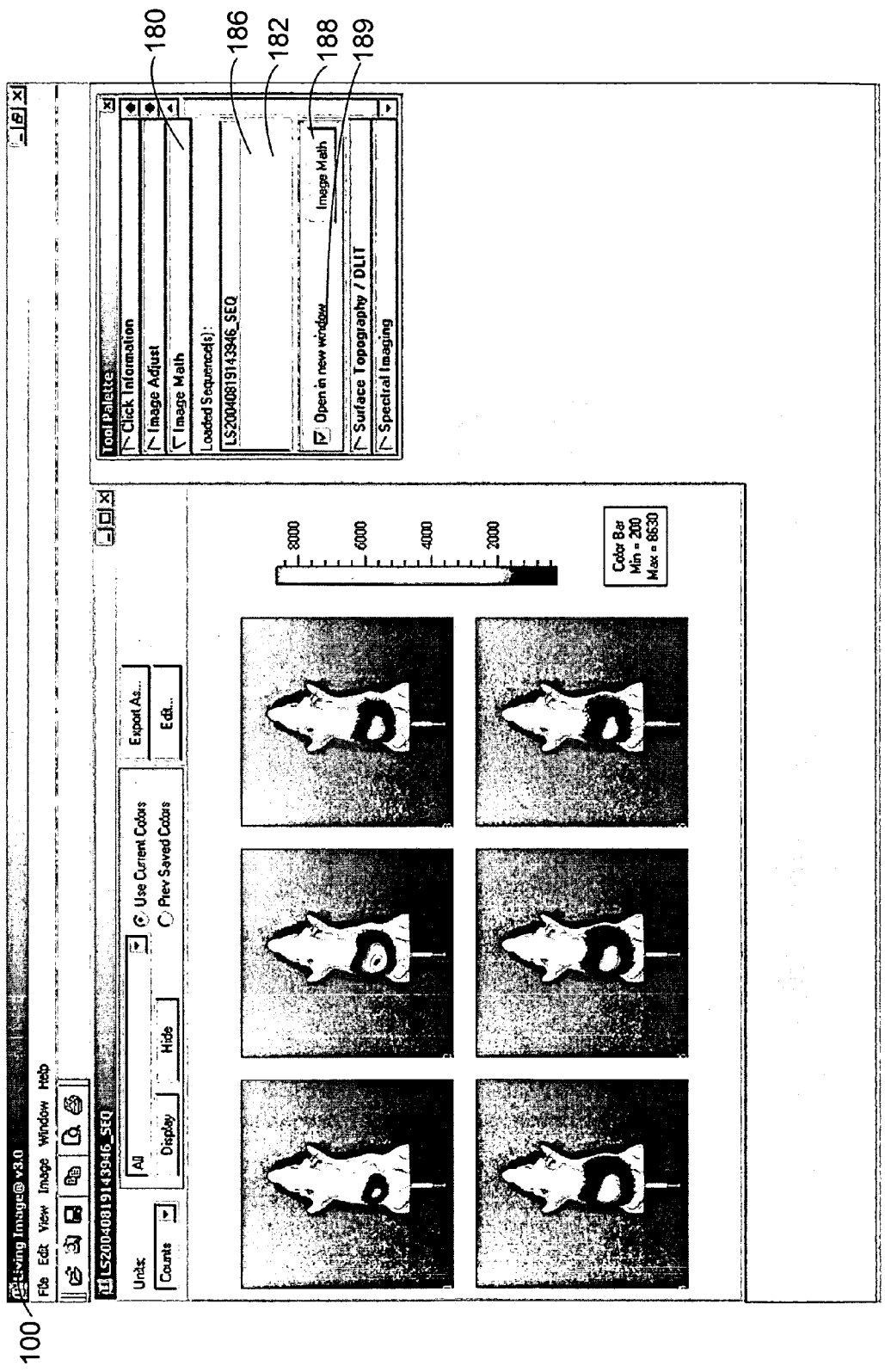
FIG. 4B illustrates an imaging GUI with an Image Math toggle enabled and showing an Image Math tools section in accordance with a specific embodiment of the present invention.

FIG. 4B illustrates GUI 100 with Image Math toggle 180 enabled and showing Image Math tools section 182 in accordance with a specific embodiment of the present invention. A window 186 displays any sequences currently opened in window 185. Image math button 188 and new window toggle 189 allow a user to evaluate two light emitting representations.

Figure 4C:
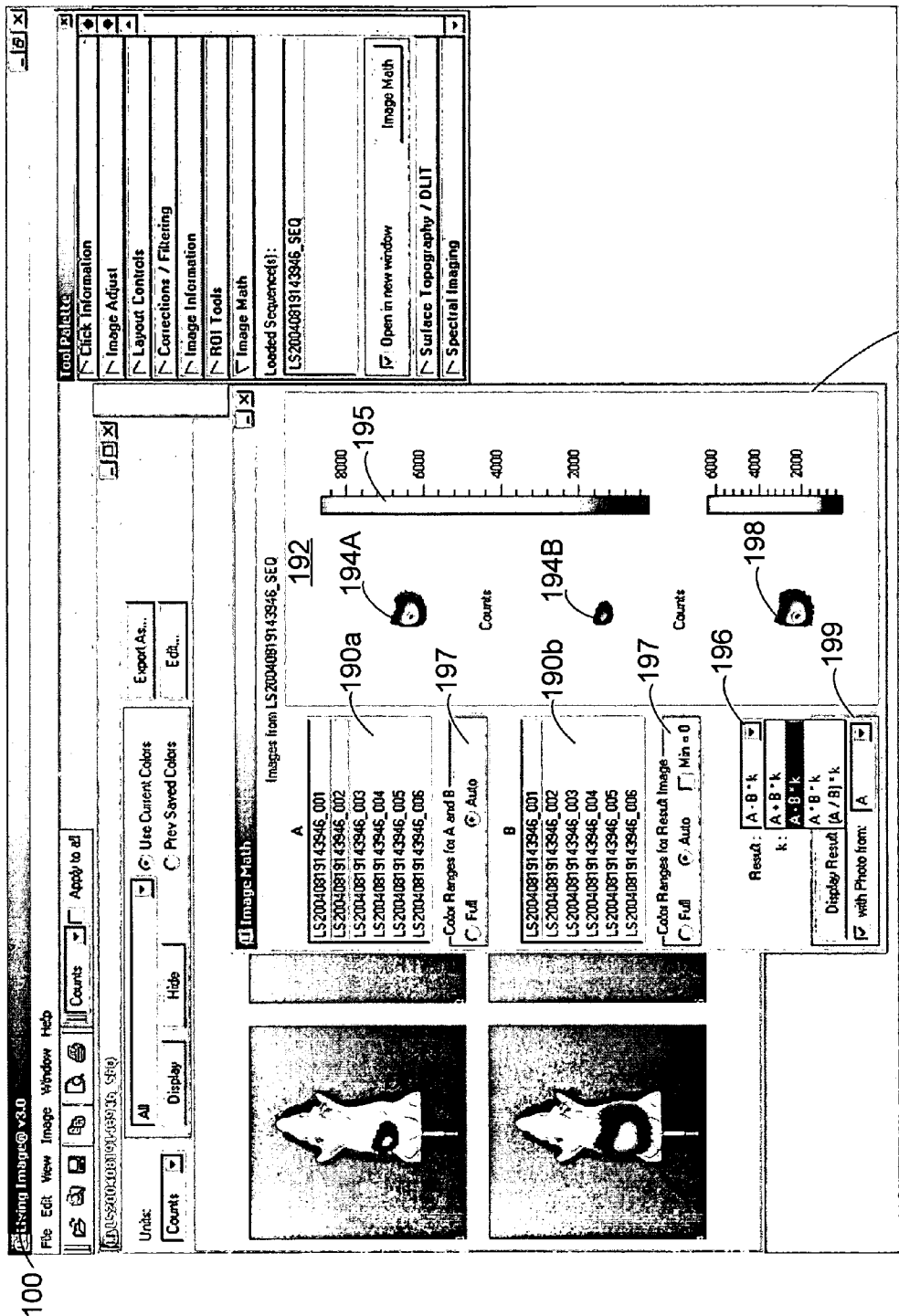
FIG. 4C illustrates an image math window that allows a user to evaluate information from a first light-emitting representation and a second light-emitting representation.

FIG. 4C illustrates an image math window 191 that allows a user to evaluate information from a first light-emitting representation and a second light-emitting representation. Window 191 appears in response to a user selecting button 188 and new window toggle 189 (as shown in FIG. 4B).

Window 191 includes two lists 190a and 190b. Each list 190 allows a user to select a light emitting representation of the object from a list of light emitting representations for the object. For example, the list may correspond to a sequence of daily images taken for the object. For convenience, the first light-emitting representation is labeled 'A' within window 191, while the second light-emitting representation is labeled 'B'. As shown, representation A includes the second luminescent image in a sequence of images, while representation B represents the first image in a sequence of images.

An evaluation tool 196 permits a user to input or select a mathematical operation for the quantitative evaluation of A and B. When a user selects mathematical operation via tool 196, GUI 100 performs a quantitative evaluation for A and B according to the mathematical operation. As shown, a user has selected a mathematical operation of subtracting A from B. Calculating the difference between the two light emitting representations permits a comparison between a previous light emitting representation, A, and a subsequent representation, B. This is useful in subtracting tissue autofluorescence from a fluorescent image. This is also useful in assessing and illustrating the progression of a pathogen in an object. Similar comparisons may be done for each day in a daily sequence. Luminescent representation 198 visually and graphically illustrates the difference between A and B. A constant, k, permits a user to amplify (or reduce) the difference between the two light emitting representations.

A pulldown window for evaluation tool 196 also permits a user to select other predetermined mathematical operations and evaluations for A and B. As shown, tool 196 permits a user to add A and B, multiply A and B and divide B by A. Generally, evaluation tool 196 may include any mathematical operation relation between A and B useful in analyzing information included in multiple light-emitting representations.

A display window 192 illustrates light emitting representations 194 for A and B and luminescent representation 198.

Luminescent scale graphic 195 provides an illustrative reference for the magnitudes of data within representations 194 and 198. Display controls such as a color range controls 197 permit a user to adjust visual output in display window 192 for A and B and luminescent representation 198.

Display tool 199 allows a user to create an overlay image (a combination luminescent image and reference image in such as a photographic image, such as FIG. 2) for the output of the quantitative evaluation.

The present invention also enables improved spectral imaging analysis and data manipulation. As the term is used herein, spectral imaging refers to any imaging that uses multiple wavelengths. Spectral imaging data can be obtained using a series of bandpass filters. The spectral imaging data provides information on the depth of a particular source, since absorption is wavelength dependent. Bandpass filters can also be used to distinguish reporters with different wavelengths. In one embodiment, the spectral imaging for GUI 100 uses a simplified model to derive internal light data information. For example, the light source may be reconstructed as a point. This expedites reconstruction and provides a simpler representation for the light source that includes flux and depth. A user may then readily read how deep and how strong the light source is within the object. In a specific embodiment, GUI 100 uses a simple slab (flat surface) model approximation to determine depth and brightness of an internal source. Other reconstruction techniques are suitable for use with spectral imaging analysis in GUI 100.

Figure 5A:
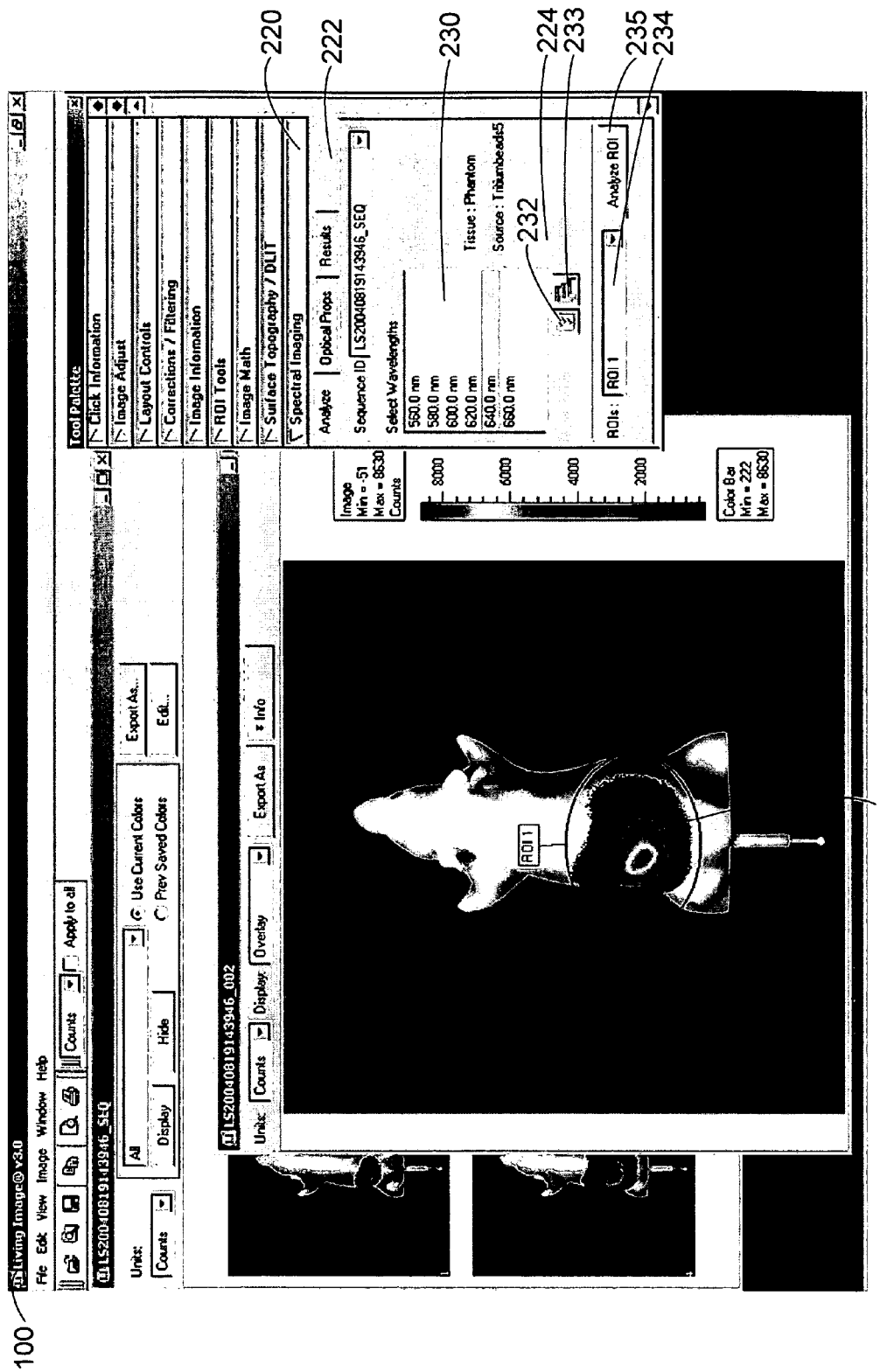
FIG. 5A illustrates an imaging GUI with a Spectral Imaging toggle enabled and showing a Spectral Imaging tools section in accordance with a specific embodiment of the present invention.

FIG. 5A illustrates GUI 100 with Spectral Imaging toggle 220 enabled and showing Spectral Imaging tools section 222 in accordance with a specific embodiment of the present invention. Spectral Imaging tools section 222 comprises a number of spectral data analysis tools that facilitate spectral imaging to determine the location and brightness of an internal light source inside an object. The spectral imaging tools may include any input that permits a user to alter or affect a reconstruction, such as altering one or more of the wavelength properties employed in an internal reconstruction. Spectral Imaging tools section 222 may also include tools that help a user interpret, analyze and display results of a reconstruction. As a result of input via Spectral Imaging tools section 222, a computer running GUI 100 performs a reconstruction for a light emitting representation according to spectral input provided by a user. Spectral Imaging tools section 222 comprises three tabbed windows: analyze window 224 (FIG. 5A), optical properties window 226 (FIG. 5B), and spectral results window 228 (FIG. 5C).

Analyze window 224 comprises a select wavelengths tool 230 that permits a user to select a wavelength for reconstruction of the light emitting representation. As shown, select wavelengths tool 230 comprises a set of predetermined wavelengths that a user may select individually or collectively (e.g., by holding a shift key for example and selecting multiple wavelengths). This allows the user to select a wavelength range for light reconstruction. Button 232 allows the user to select all wavelengths in window tool 230. One of skill in the art is aware of the benefits of imaging with varying and/or multiple wavelengths. For example, an imaging apparatus may take luminescence images of an object at different wavelengths to overcome dependency on depth of the image, to compensate for different sized specimens or images at varying depths. Wavelength tool 230 allows a user to reconstruct internal luminescent data flexibly at one or more wavelengths.

ROI tool 234 allows a user to select which region of interest the spectral analysis will occur upon, if multiple ROIs have been created. ROI tool 234 comprises a pulldown menu that lists each region of interest created in ROI tools section 162 and/or previously stored for the current luminescent image 108.

Analyze ROI button 235 causes the computer system running GUI 100 to perform a reconstruction for light emitting representation 108 according to the user input in spectral imaging tools section 222. In one embodiment, spectral reconstruction for light emitting representation 108 using ROI button 235 produces a point light source within the object. Display toggle 233 allows a user to create a separate window that displays the results of spectral analysis for each wavelength (if multiple wavelengths have been selected within wavelength window 230).

Figure 5B:
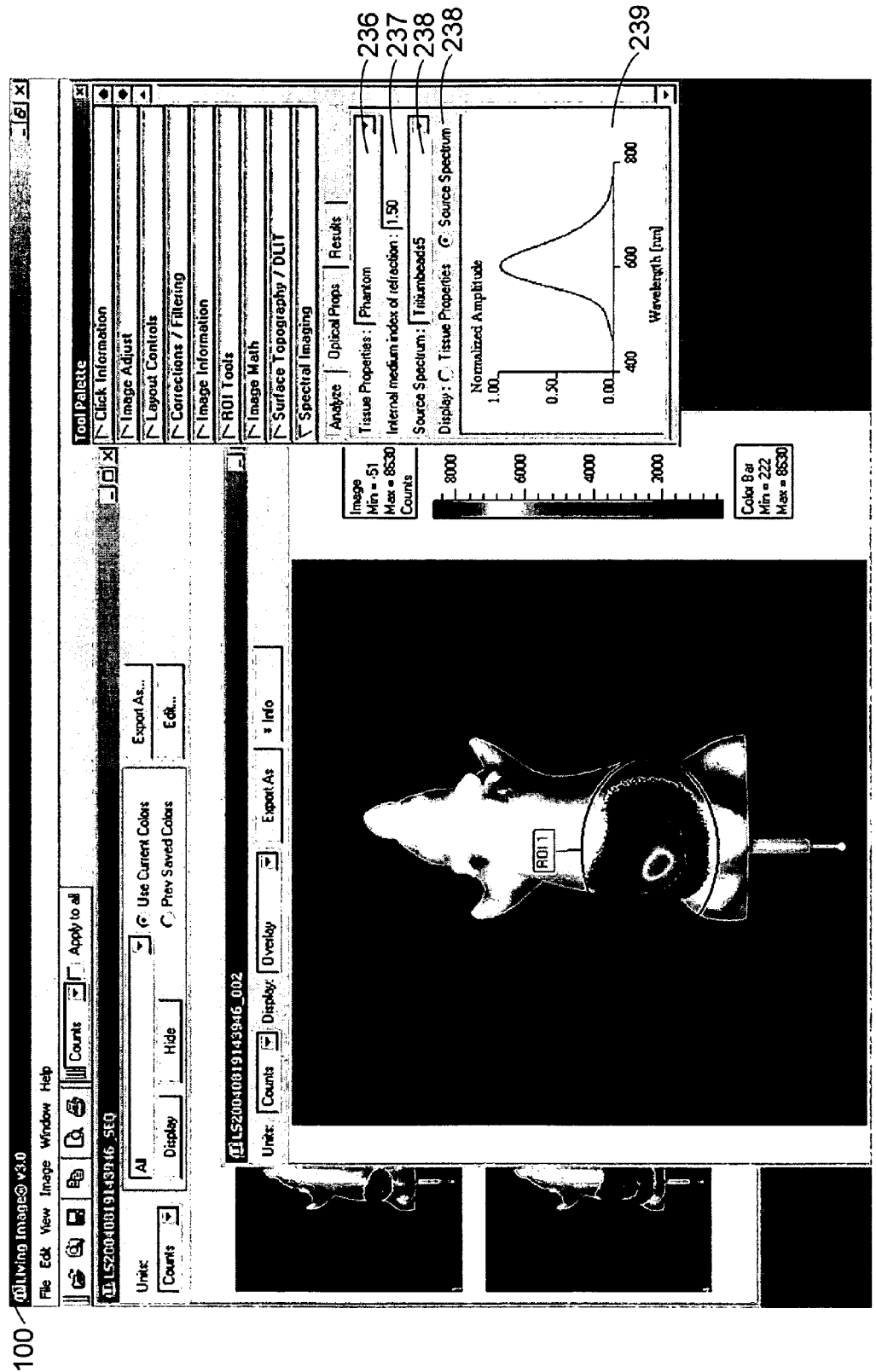
FIG. 5B illustrates spectral analysis tools included in an optical properties window.
Figure 5C:
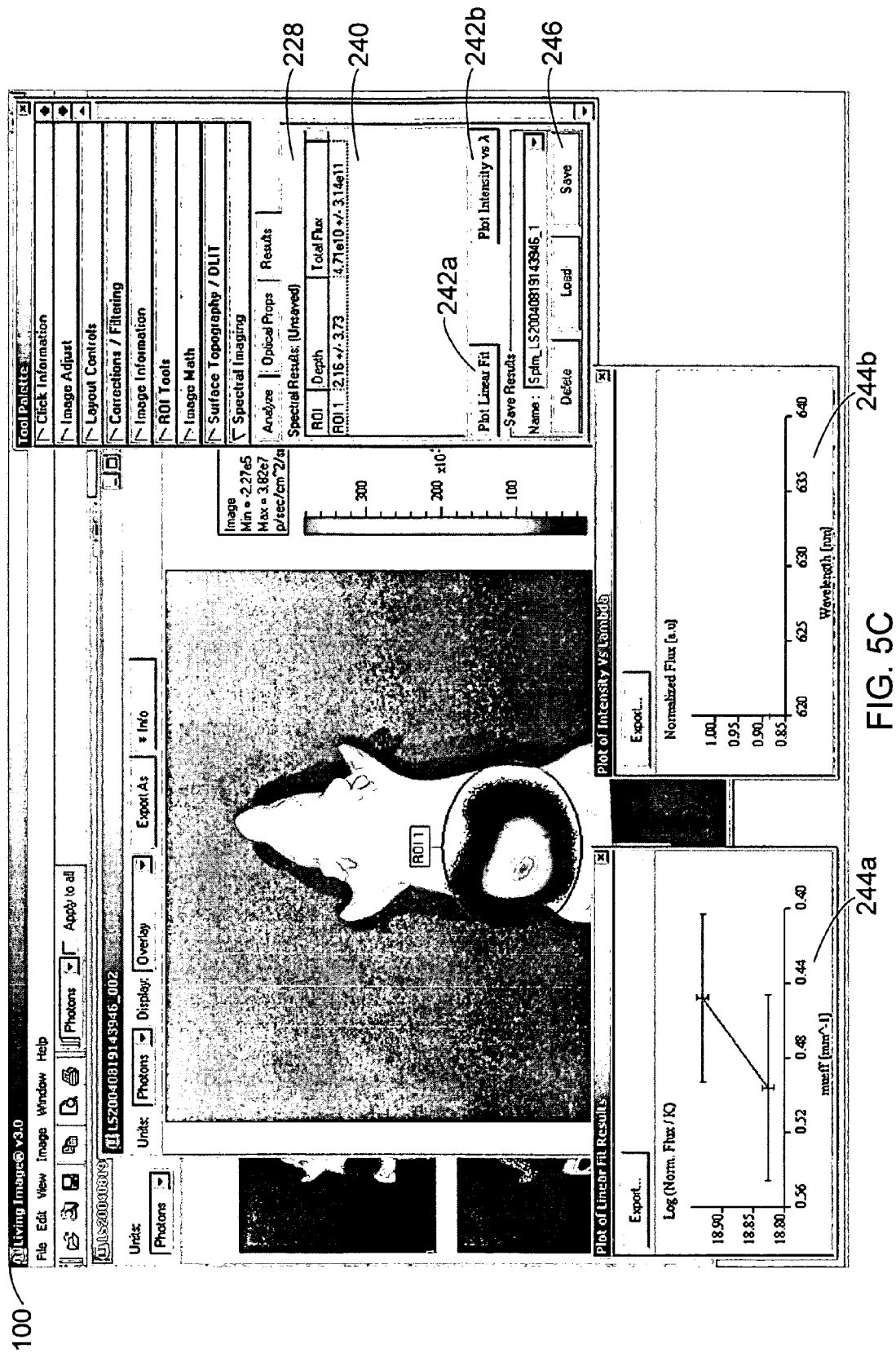
FIG. 5C illustrates several spectral analysis tools included in a spectral results window.

FIG. 5B illustrates additional spectral analysis tools included in optical properties window 226. Input from tissue properties tool 236 permits a user to select a tissue property model for reconstruction of the light emitting representation 108. In this case, GUI 100 includes several stored tissue property models listed in a pulldown menu 236. Each model includes stored values that cumulatively represent the optical behavior of a volumetric medium that represents a portion of the object and contains the light source for reconstruction. Exemplary models may include a mammalian tissue model, a mouse model, a phantom (a plastic representation of tissue), a subcutaneous model, a lower body model, and a specific model that corresponds to a particular object being imaged.

Input from light source spectrum tool 238 permits a user to designate a representative spectrum for an internal light source within mammal 109 for a reconstruction. In this case, GUI 100 includes several stored spectrum representations listed in a pulldown menu 238. Each spectrum representation mathematically corresponds to a spectral emissions profile for a light source. Exemplary light source and spectrum representations may include spectrum representations for: luciferase, a fluorescent marker or dye, tritium beads, an LED light source used within a test device, etc.

A display window 239 illustrates either a current tissue property selected with tool 236 or a light source spectrum selected via tool 238. As shown, display window 239 illustrates a normalized amplitude response for tritium beads as a function of wavelength. A display for each tissue property in tool 236 may include a graph of one or more optical coefficients vs. wavelength, for example.

FIG. 5C illustrates several spectral analysis tools included in results window 228. An ROI results window 240 displays basic results of a reconstruction performed by the computer when prompted using analyze ROI tool 235 (FIG. 5A). Specifically, window 240 lists each ROI for the luminescent image 108, along with information related to the light source within object 109 such as a reconstructed location (e.g., depth from a surface and/or 3-D position) and magnitude (e.g., luminous flux, size in cells, watts, etc.) for the light source.

Results window 228 also includes one or more plot tools 242 which when selected by a user graphically illustrate information related to the reconstruction. Two such exemplary tools 242 are illustrated: a plot linear fit button 242a and a plot intensity verse wavelength button 242b. Selecting each tool 242a and 242b causes a separate window 244a and 244b, respectively, to open on the display. Save tools 246 permit a user to save results from a reconstruction, including parameters set using tools in analyze window 224 and optical properties window 226.

GUI 100 may also include other spectral analysis tools that permit a user to affect reconstruction of an internal light source. For example, tool 237 permits a user to specify an internal medium index of refraction for a spectral reconstruction. Other spectral analysis tools are contemplated for use with GUI 100.

Figure 6A:
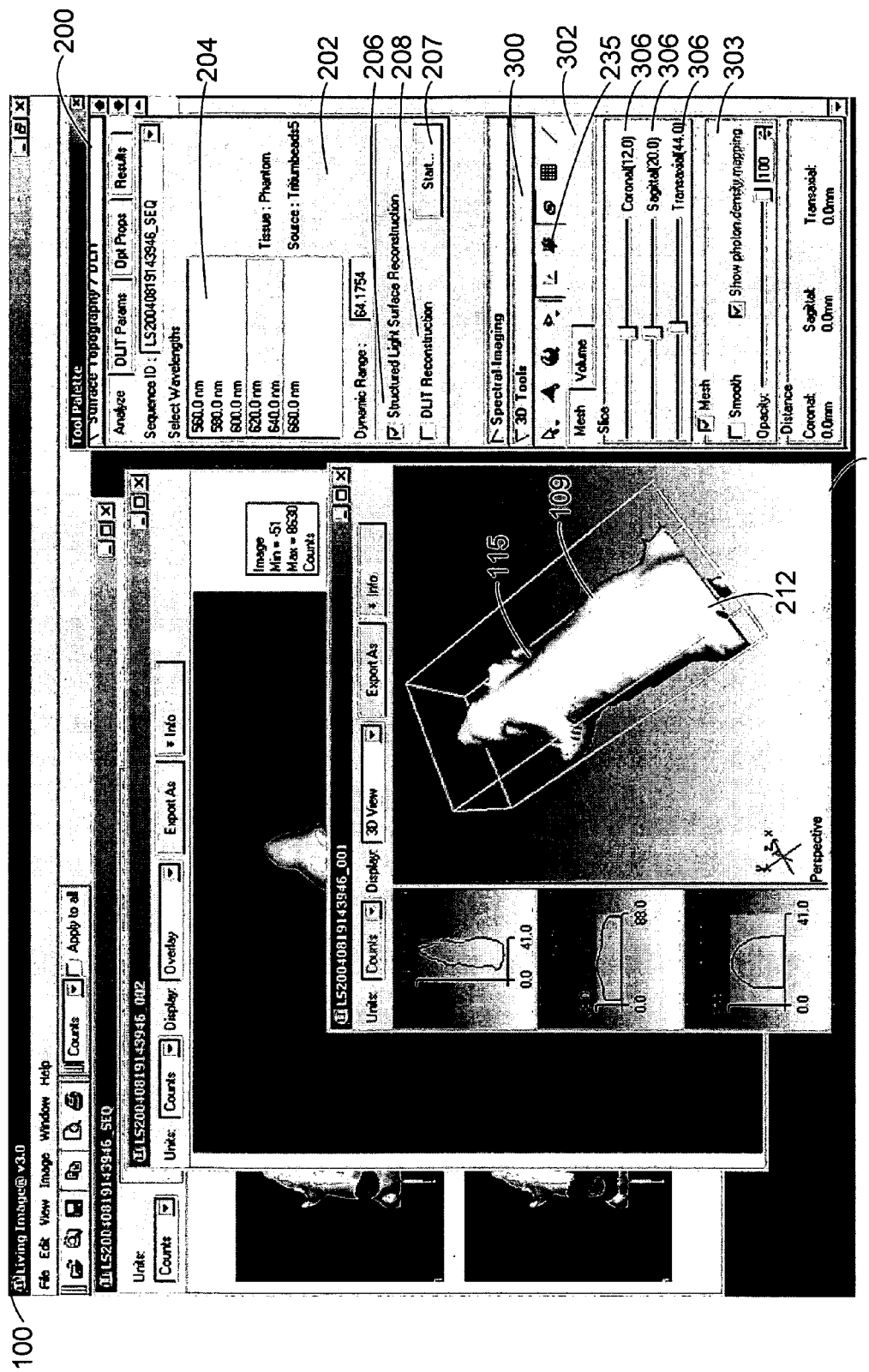
FIG. 6A illustrates an imaging GUI with Surface Topography and reconstruction tools in accordance with a specific embodiment of the present invention.

FIG. 6A illustrates GUI 100 with Surface Topography/DLIT toggle 200 enabled and showing Surface Topography/DLIT tools section 202 in accordance with a specific embodiment of the present invention.

As a result of user input, GUI 100 causes a processing system to perform a reconstruction for a light emitting representation according to input provided by the user. As the terms are used herein, 'reconstruct' and 'construct' and 'build' (and their derivatives) are used interchangeably and generally denote mathematical assembly of a representation and its related information using a set of input data and a mathematical model. Typically, the computer system builds a 2-D or 3-D digital representation of a light source internal to the object (mammal, test device, etc.) using a) data included in one or more images, b) any user input, and c) a computer-implemented reconstruction model. There are a wide variety of reconstruction models suitable for use with the present invention.

In one embodiment, the reconstruction is a tomographic reconstruction. In this case, GUI 100 employs a quantitative model that estimates the diffusion of photons in tissue. In a specific embodiment, the model processes in vivo image data and spatial resolution as a function of depth, and also helps define requirements of imaging components during image capture. Various diffusion and reconstruction models may be implemented by GUI 100 to represent photon propagation through a mammalian subject or a test device. One suitable example of software that builds a digital representation of a light source internal to a mammal or test device using data from one or more images is described in commonly owned and pending patent application Ser. No. 10/606,976 entitled "Method and Apparatus for 3-D Imaging of Internal Light Sources" and naming Brad Rice et al. as inventors. This application is incorporated by reference herein and its entirety for all purposes.

In the case where scattering is large compared with absorption, such as red to near-infrared light passing through tissue or a phantom device that comprises an optically selective material configured to resemble tissue, the transport of light within the sample may be described by diffusion theory; In this case, the computer-implemented reconstruction model implements a diffusion model to build the light source digital representation. One 3-D diffusion software implementation reconstructs light data internal to an object surface based on the surface light image data. In this case, the image and surface light data is converted into photon density just below the phantom device surface, and this photon density is used to produce 3-D light data internal to the object surface including the light source.

Building a digital representation for the light source may rely on assumptions or estimates of optical properties for the object. For example, reconstructing the digital representation of the light source may employ a) an optical scattering representation for mammalian tissue or an optically selective material used in a phantom device, and b) an optical absorption representation for the tissue or optically selective material at one or more wavelengths. Several representations are stored in memory and provided to the reconstruction algorithm according to user selection via tools 236 and 238 (FIG. 5B) or tools 236 and 238 (FIG. 5B).

The resulting digital representation of the light source may include information that includes mathematical descriptions of: an estimated intensity of the light source, an estimated location of the light source within the phantom device, and/or an estimated size or shape of the light source. In one embodiment, the light source is reconstructed as a complex source characterized spatially in three dimensions. This reconstruction uses surface topography of the object and produces a light source with 3-D information such as size, orientation and shape. In another embodiment, the light source is reconstructed as a point.

Figure 6B:
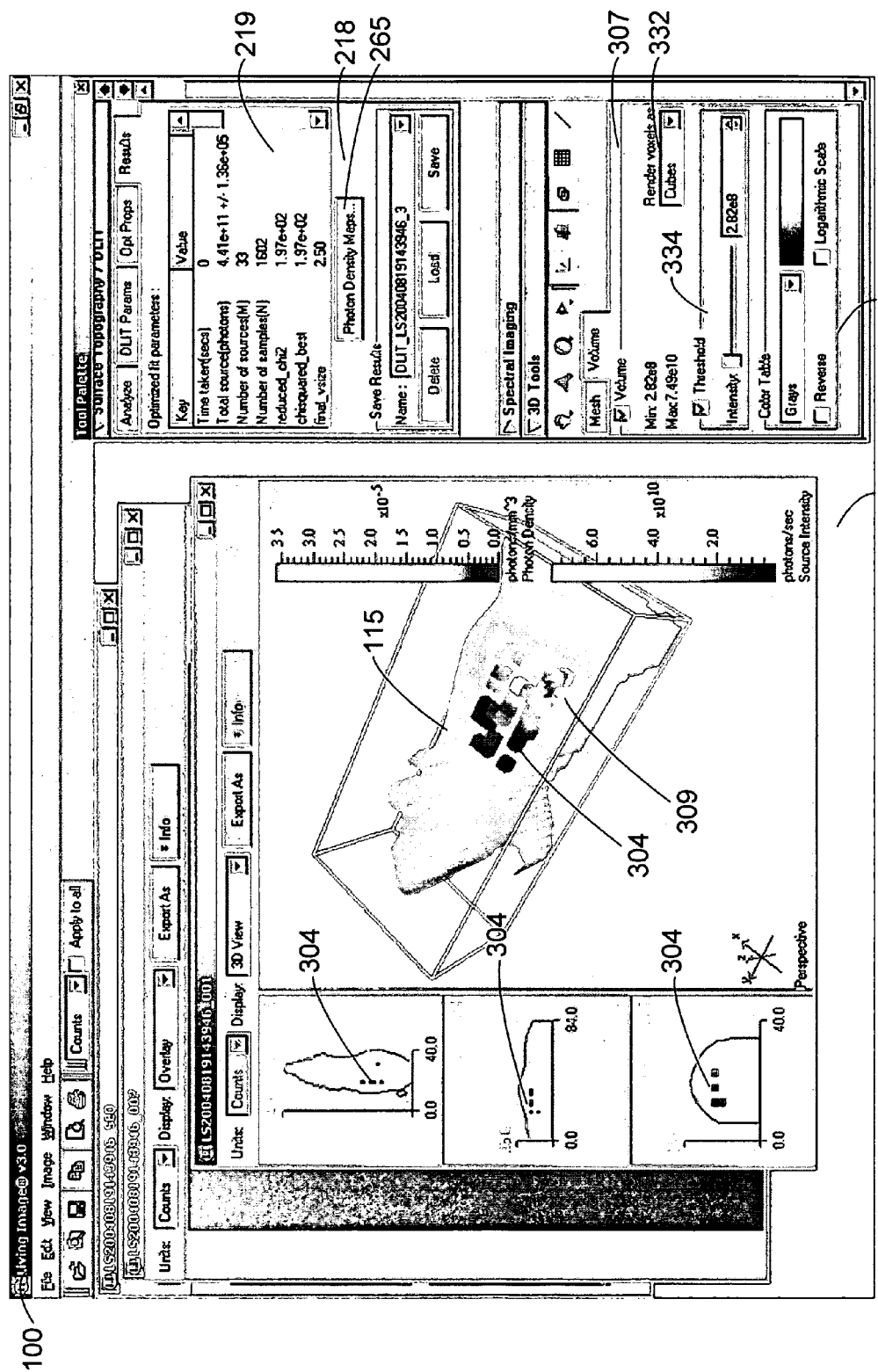
FIG. 6B shows a top perspective view of an object and internal light source after topographic and tomographic reconstruction.

Surface Topography/DLIT tools section 202 includes numerous tools for 3-D topographic and tomographic reconstruction of object 109. Section 202 is divided into four tabbed windows: analyze window 202 (FIG. 6A), DLIT parameters window 212 (FIG. 6C), optical properties window 214 (FIG. 6D), and reconstruction results window 218 (FIG. 6B).

Initially referring to FIG. 6A, when a user selects topographic representation tool 206, the computer system running GUI 100 builds a 3-D topographic representation (a surface map) of the object. In this case, tool 206 comprises a checkbox 206 and a start button 207 that initiates the topographic reconstruction of object 109. In one embodiment, the computer system employs structured light data from one or more structured light images in building the topographic representation. After reconstruction is complete, GUI 100 creates a separate window 210 for the 3-D topographic reconstruction. Window 210 comprises a pictorial display of the topographic representation 212.

In response to a user selecting topographic representation tool 206, GUI 100 also creates a new 3D Tools tab 300 in tool palette 102. Activating 3D Tools tab 300 opens 3D Tools section 302. 3D Tools section 302 includes one or more tools that permit a user to analyze 3-D imaging information and the topographic representation 212 of object 109 presented in window 210. 3D Tools section 302 will be discussed in further detail below.

Surface Topography/DLIT tools section 202 also includes a 3-D reconstruction tool 208. When a user selects reconstruction tool 208, the computer system builds a three-dimensional representation of a light source internal to object 109. Typically, this involves performing a three-dimensional tomographic reconstruction of the light source internal to the object. In this case, tool 208 comprises a checkbox 208 and a start button 207 that initiates the tomographic reconstruction of a light source internal to object 109.

GUI 100 uniquely and flexibly permits display and manipulation of multiple types of 3-D information. 3-D representations of data useful for in-vivo imaging may include surface mesh and internal voxel data. In one embodiment, the surface mesh data is derived from structured light information obtained for an object using a camera and a structured light generator. The surface mesh data is also referred to as surface topography data. The internal light intensity data comes from a calculation of internal volume elements (or 'voxels'), e.g., using diffuse tomography, and provides light intensity in each volume element. The present invention advantageously lets a viewer see both surface mesh and internal volume element 3-D representations of data and vary the display of each relative to each other. By contrast, many conventional systems only show one or the other. For example, an MRI solely shows internal voxel (or volume) data. In addition, GUI 100 may display measured light intensity (or photon density) mapped onto a surface.

Figure 6C:
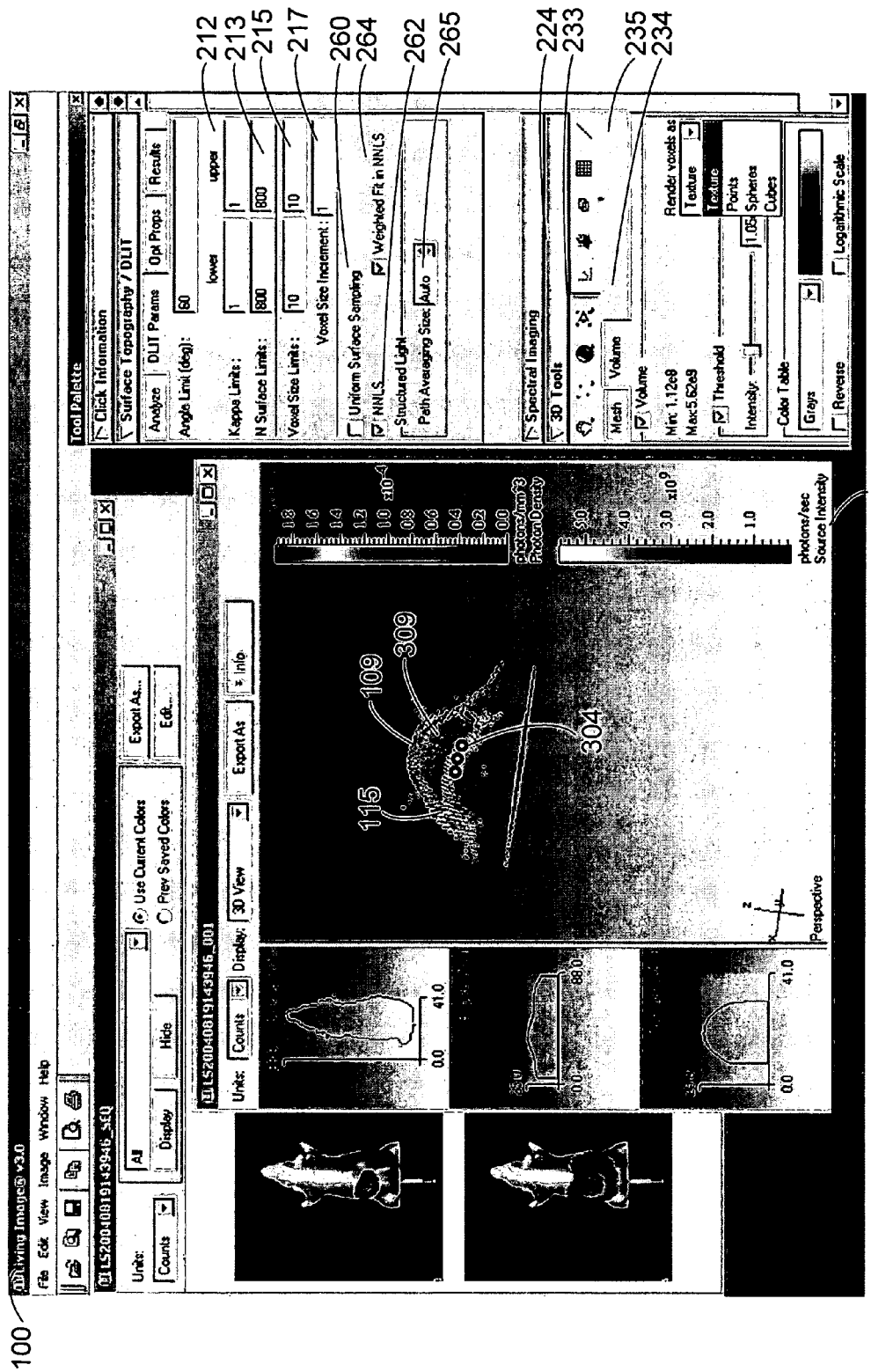
FIG. 6C shows a back view of the object, displayed in a pointcloud drawing style, that shows depth of an internal radiation source and a projection of the internal radiation source to a surface emission on the top surface of a topographic representation.
Figure 6D:
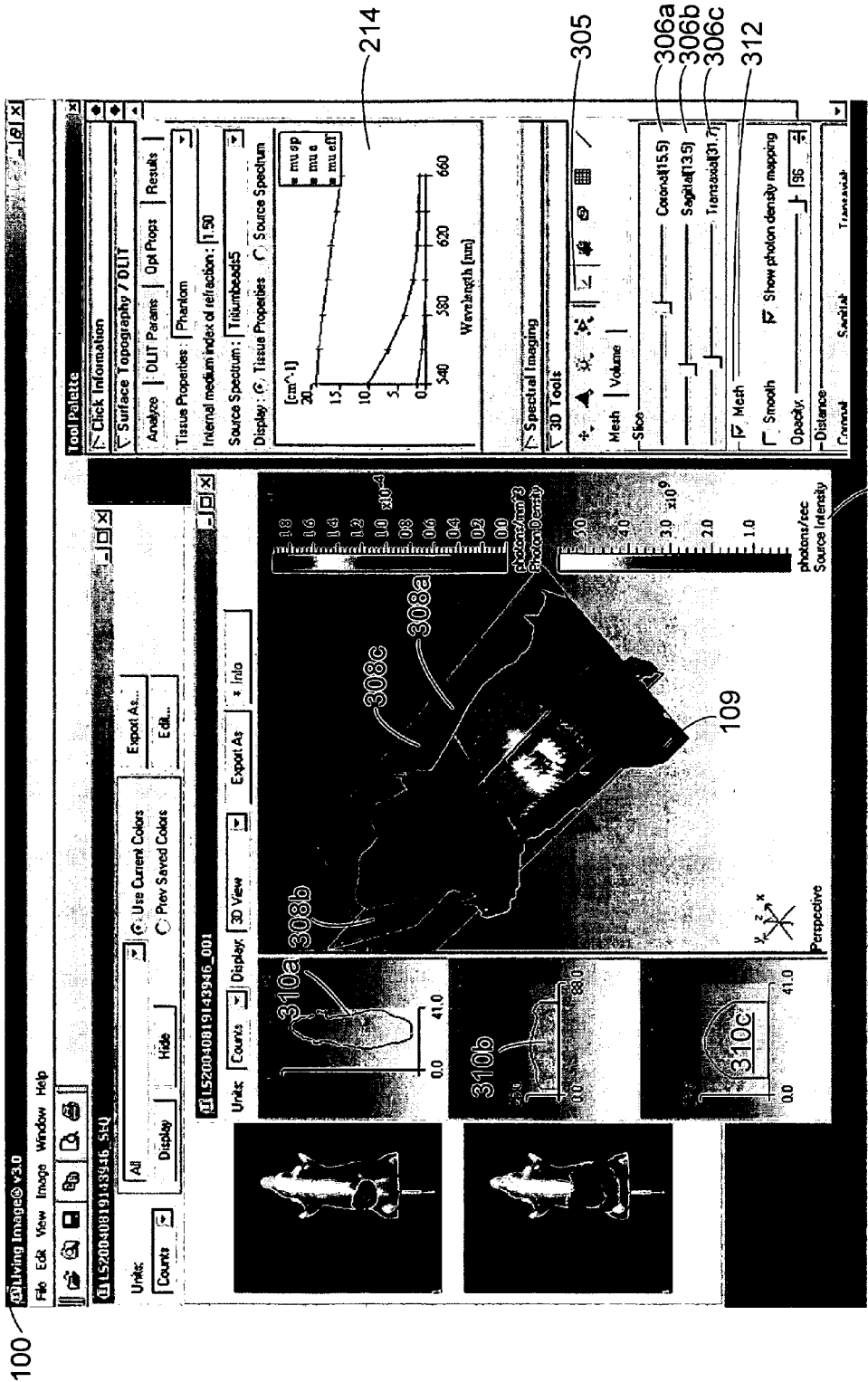
FIG. 6D illustrates an optical properties window, which comprises several spectral analysis tools that permit a user to designate one or more optical properties for a reconstruction.

FIGS. 6B, 6C and 6D illustrate exemplary three-dimensional output of reconstruction 208 in window 210. FIG. 6C shows a back view of object 109 (displayed in a pixilated drawings style) that shows depth of internal light source 304 and a projection of the internal light source 304 to a surface emission 309 on the top surface of object 109 as received by a camera. Thus, FIG. 6C shows a surface representation 115, internal light source representation 304 and projection 109 of source 304 on the surface. FIG. 6B shows a top perspective view of object 109 (displayed in a solid drawings style) and the surface emission 309 of an internal light source 304 mapped onto a 3-D tomographic representation 115. FIG. 6D shows a top perspective view of object 109 (displayed in a solid drawings style) with coronal, sagittal and transaxial planes drawn through object 109.

Thus, GUI 100 lets a user display several types of 3-D visualizations in one image. More specifically, FIG. 6B simultaneously shows: 1) a surface mesh 115; 2) a photon density 309 on the surface, represented by a pseudo-color scale; 3) the locations of voxels 304 with non-zero (for example >2%) light intensity inside the volume; 4) the intensity of voxels represented by another pseudo-color scale (generally indicated by the legend for luminescence image display section 107). In one embodiment, the tomographic reconstruction also uses spectral imaging and parameters. Referring back to FIG. 6A, analyze window 202 comprises a wavelength selection window 204 that allows a user to select one or more wavelengths for a tomographic reconstruction initiated by reconstruction tool 208. For example, using a mouse or similar input device, the user may create a box and select 1, 2 or more wavelengths presented within window 204.

Referring to FIG. 6C, DLIT parameters window 212 comprises several tools that permit a user to alter a reconstruction parameter for tomographic reconstruction. Windows 213 allow a user to set a number of surface elements used in the tomographic reconstruction. Windows 215 allow a user to set a number of internal volume elements used in the tomographic reconstruction. The user may also set an increment for volume mesh reconfiguration using window 217, which is useful when the tomographic reconstruction employs an iterative approach for volume mesh size. A checkbox 260 permits a user to designate whether uniform surface sizes are used in the reconstruction. In one embodiment, a tomographic reconstruction employs a least squared fit to derive a solution that represents the internal light source. Checkboxes 262 and 264 allow user to influence how a least squared fit and solution is implemented (e.g., enabling a non-negative least squares fit). DLIT parameters window 212 also includes a window 265 that permits a user to specify the average size of a path used in structured light representation for tomographic reconstruction. Also, as shown, a user may also set angular limits for reconstruction and a value for one or more constants or variables (kappa) employed in the mathematical reconstruction.

FIG. 6D illustrates optical properties window 214, which comprises several spectral analysis tools that permit a user to designate one or more optical properties for a reconstruction. Optical properties window 214 is similar to optical properties window 226 of FIG. 5B and includes similar tools that allow a user to designate optical tissue properties, a light source spectrum and a medium index of refraction, each of which affects reconstruction of the internal light source using reconstruction tool 208. A user interacts with tools within optical properties window 214 similar to that described above with respect to window 226 and will not be described again for sake of brevity.

Reconstruction results window 218 (FIG. 6B) includes a sub-window 219 that lists results of a reconstruction performed by the computer system and initiated via reconstruction tool 208. Generally speaking, window 219 may list any result from the reconstruction or parameter used in the reconstruction. When a user selects photon density maps button 265, GUI 100 opens a new window (not shown) that graphically displays the difference between the measured and simulated optical data for light representation of object 109.

As mentioned above, 3D Tools section 302 includes several graphical instruments that permit a user to analyze the topographic/tomographic representation of object 109. Section 302 comprises two tabbed windows: mesh window 303 (FIGS. 6A, D and 6E) and volume window 307 (FIGS. 6B and 6C). The mesh tab controls visualization of the surface topography, or surface mesh. The volume tab controls display of the light source points/voxels internal to the surface. Three orthogonal slices 308a-c are included to provide a user with shape characterization of object 109 according to a plane defined by each slice. A toggle 305 turns the slices 308 on (FIGS. 6D and 6E) and off (FIGS. 6A-C). As shown in FIG. 6D, orthogonal slices 308a-c are displayed in window 210. A sub-window 310a-c within window 210 is also included for each orthogonal slice 308a-c, respectively. Each sub-window 310 displays the perimeter profile of object 109 according to the current position of its respective slice 308. Sliders 306a-c control the position of each slice 308a-c, respectively. Slices 308 also provided spatial three-dimensional volume information based on their current position.

Orthogonal slices 308a-c also show intersecting volume data according to their current position. In a specific embodiment, slices 308a-c show intersecting voxels with light intensity above zero (or another threshold). FIG. 6B illustrates slices 308a-c located to intersect with internal light information 304. The light information is shown as points corresponding to individual volume elements in sub-windows 310a-c. Thus, depending on position of each slice, these slice tools may not only show the surface shape at a particular plane, but they show the intersecting volume data. In other words, they show voxels with a light intensity above zero or some other predetermined threshold.

Figure 6E:
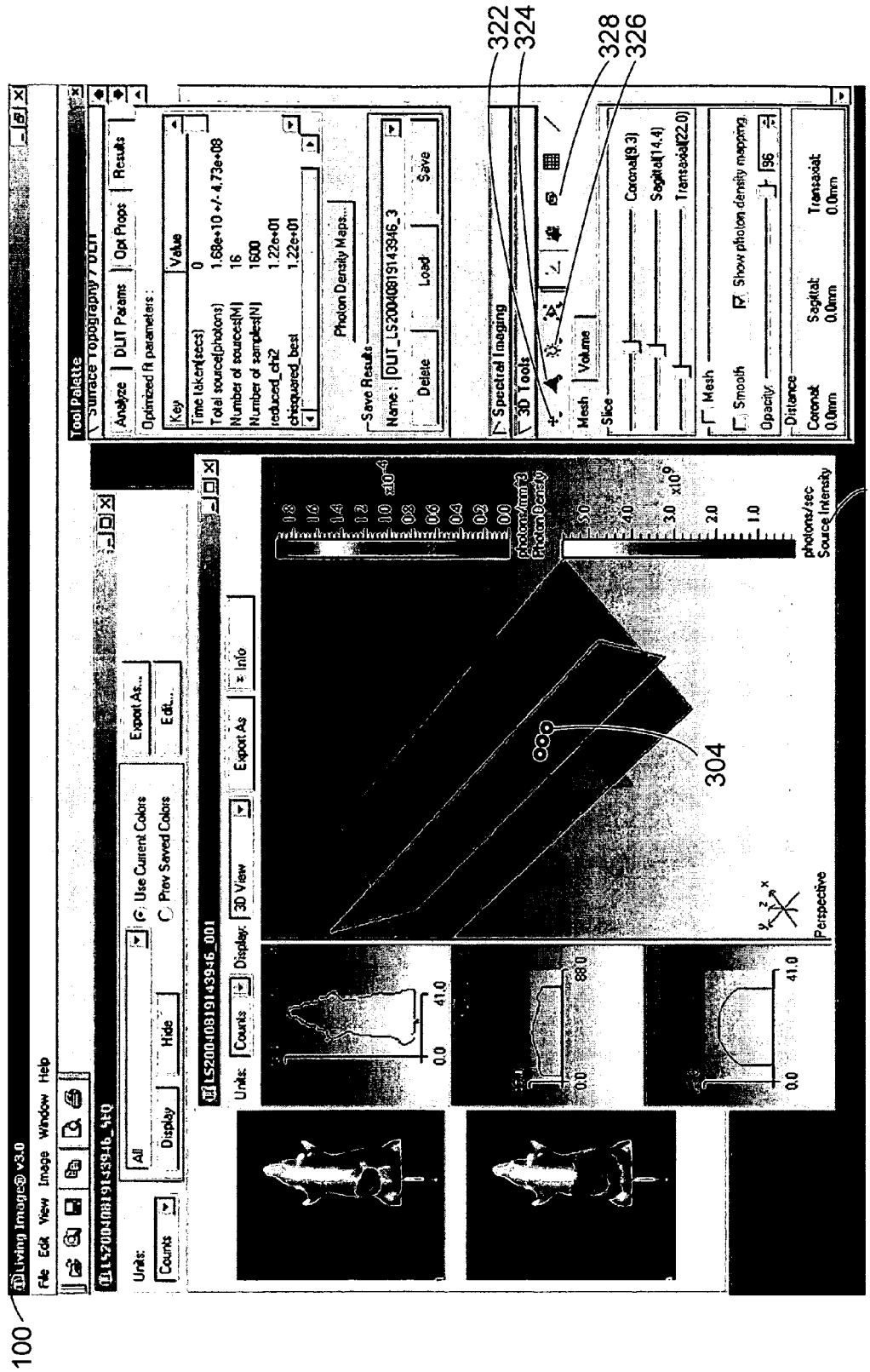
FIG. 6E shows reconstructed internal light sources without a topographic representation.

3D Tools section 302 also includes various tools for manipulating the presentation and position of topographic representation 115 in window 210. Pulldown menu 322 permits a user to control the orientation, position or viewing angle of topographic representation 115. Pulldown menu 324 permits a user to designate a drawing style for topographic representation 115. Exemplary drawings styles include a wire mesh representation, a surface node representation (FIG. 6C), a volume-based representation (FIG. 6A), etc. Pulldown menu 326 permits user to designate the lighting conditions for viewing topographic representation 115. Bounding box button 328 disposes a box about the topographic representation 115 (FIG. 6A). Mesh toggle 312 permits a user to turn on and off the topographic representation. FIG. 6E illustrates the internal light sources 304 without a topographic representation 115 of object 109 and only including the internal light sources—as reconstructed from surface image data obtained by a camera.

Referring to FIG. 6B, volume window 307 comprises various tools that allow a user to vary volumetric presentation of object 109, such as legend control and visual output tools 330, intensity threshold tool 334, and voxel rendering pulldown menu 332. Voxel rendering pulldown menu 332 lets a user select how internal volume data is presented. Four options are provided by pulldown menu 332: texture, points, spheres and cubes. Other options are contemplated to facilitate the illustration of internal data. FIG. 6C shows point voxel rendering, which pinpoints precise location of internal light data. FIG. 6B shows cube voxel rendering, which displays the internal volume data bigger and brighter and often easier to see in an overlay image. FIG. 6D shows texture voxel rendering, which smooths out the voxel data and is suitable when there are a large number of points, e.g., in a kidney or other macro structure.

GUI 100 may be used for imaging a low intensity light source, such as luminescence from luciferase-expressing cells, fluorescence from fluorescing molecules, and the like. The low intensity light source may be included in any of a variety of living or non-living light-emitting samples. Non-living light-emitting samples may include calibration devices and testing devices. Living light-emitting samples may include, for example, animals or plants containing light-emitting molecules, tissue culture plates containing living organisms, and multi-well plates (including 96, 384 and 864 well plates) containing living organisms. Animals may include any mammal, such as a mouse or rat containing luciferase-expressing cells.

GUI 100 finds wide use in imaging and research. The ability to track light-emitting cells in small laboratory animal such as a mouse opens up a wide range of applications in pharmaceutical and toxilogical research. These include in vivo monitoring of infectious diseases, tumor growth in metastases, transgene expression, compound toxicity, and viral infection or delivery systems for gene therapy. The ability to detect signals in real-time and in living animals means that the progression of a disease or biological process can be studied throughout an experiment with the same set of animals without a need to sacrifice for each data point. This results in higher-quality data using fewer animals and speeds the process of screening compounds leading to more rapid drug discovery.

As the term is used herein, a tool refers to any single graphical instrument or combination of graphics controls that permit a user to input information to a computer system. Common conventional graphical tools include buttons, text boxes, scroll bars, pictures, spin dials, list boxes, select options, etc. For example, a check box is a select option control tool that comprises an empty box. When a user selects the box, it is filled with an "X" or other visual information to indicate that the user has selected an option corresponding to the box. For example, one or more check boxes may be used to allow a user to quickly select from one or more predetermined tissue properties for spectral imaging, such as those listed above.

The present invention employs some form of computer system that is capable of displaying an image and analyzing data included in the image. At the least, the computer system comprises one or more processors, one or more user input devices, a display, and a graphical user interface running on one or more of the processors. The display is capable of displaying photographic, structured light, and luminescent light data images and associated information in particular ways responsive to input signals from the input devices and signals from one or more of the processors. The processors execute, based on store instructions, topographic and tomographic reconstruction algorithms as well as GUI 100.

Figure 7A:
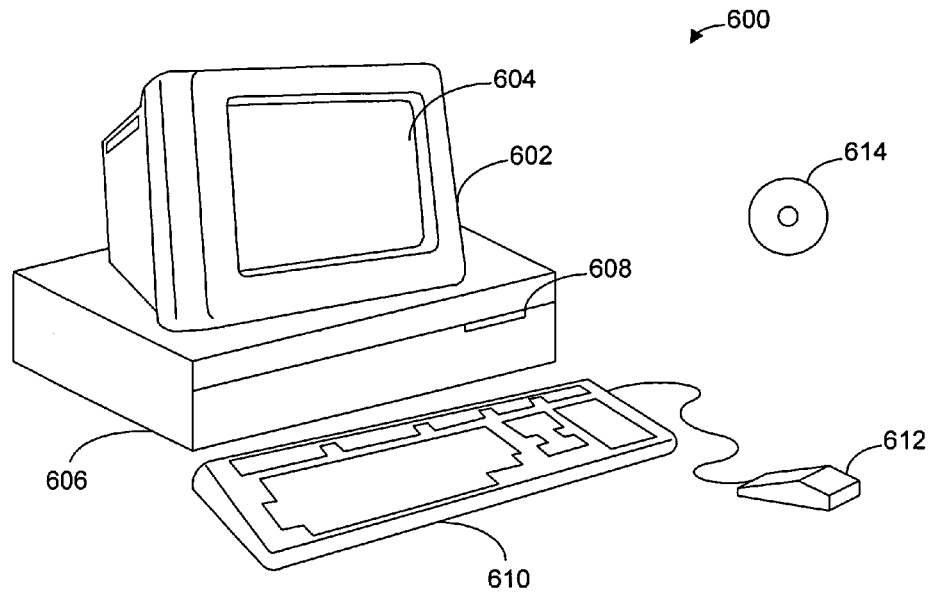
FIGS. 7A and 7B illustrate a computer system suitable for implementing embodiments of the present invention.
Figure 7B:
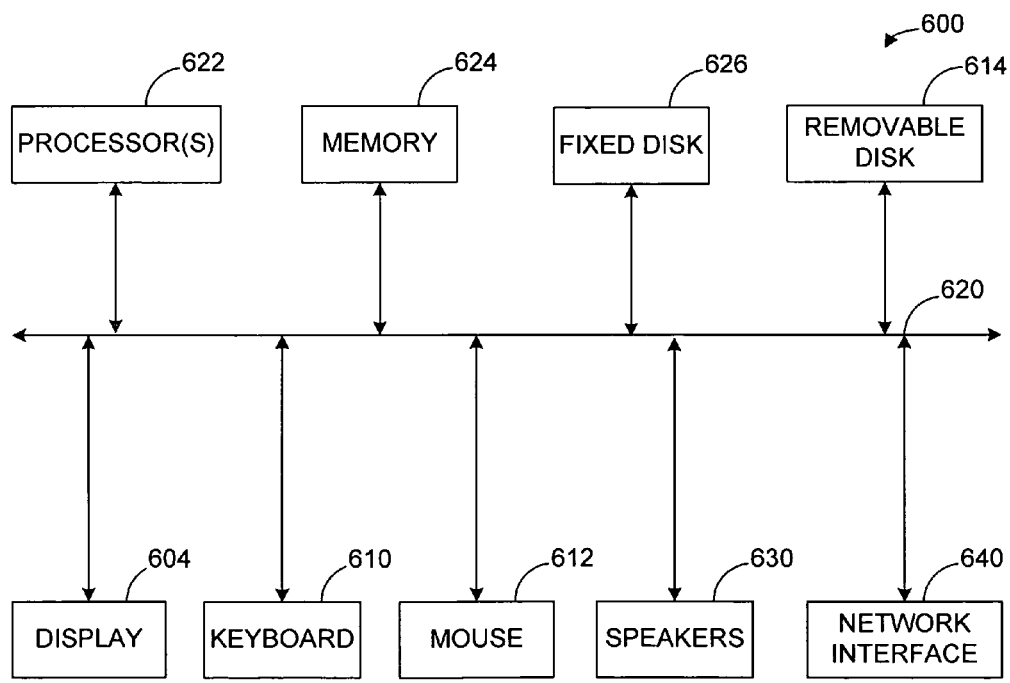

FIGS. 7A and 7B illustrate a computer system 600 suitable for implementing embodiments of the present invention. FIG. 7A shows one possible physical form of the computer system. Of course, the computer system may have many physical forms ranging from an integrated circuit, a printed circuit board, a small handheld device to the latest commercially available model. Computer system 600 includes a CRT monitor 602, display 604, housing 606, CD drive 608, keyboard 610 and mouse 612. Disk 614 is a computer-readable medium used to transfer data to and from computer system 600. Display 604 generally refers to video output provided by a display technology, such as a CRT monitor, LCD screen, projector, OLED device, and the like.

FIG. 7B is an example of a block diagram for computer system 600. Attached to system bus 620 are a wide variety of subsystems. Processor(s) 622 (also referred to as central processing units, or CPUs) are coupled to storage devices including memory 624. Memory 624 includes random access memory (RAM) and read-only memory (ROM). As is well known in the art, ROM acts to transfer data and instructions uni-directionally to the CPU and RAM is used typically to transfer data and instructions in a bi-directional manner. A fixed disk 626 is also coupled bi-directionally to CPU 622; it provides additional data storage capacity and may also include any suitable computer-readable media. Fixed disk 626 may be used to store topographic and tomographic reconstruction programs, instructions that represent and operate GUI 100, imaging data and the like and is typically a secondary storage medium (such as a hard disk) that is slower than primary storage. Removable disk 614 may take the form of any of the computer-readable media described below.

CPU 622 is also coupled to a variety of input/output devices such as display 604, keyboard 610, mouse 612 and speakers 630. CPU 622 cooperates with the input/output devices and display 604 to implement GUI 100 described above. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 622 optionally may be coupled to another computer or telecommunications network using network interface 640.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter. In one embodiment, the present invention is stored as instructions in one or more programs written in C or C++, for example.

Although the foregoing invention has been described in some detail for purposes of clarity of understanding, it will be apparent that certain changes and modifications may be practiced within the scope of the appended claims. For instance, although the present invention has been described with respect to a separate tool palette 102 and independent windows created for many tools, it is understood that the present invention may need not display numerous independent windows and some windows may be combined. Therefore, the present examples are to be considered as illustrative and not restrictive, and the invention is not to be limited to the details given herein, but may be modified within the scope of the appended claims.

What is claimed is:

1. A computer system configured to display and analyze an image including three-dimensional data of an object surface and three-dimensional light data of light emitted from within the object, the computer system comprising:
one or more processors; one or more user input devices; a display configured to display the image and associated information in particular ways responsive to input signals from one or more of the input devices and signals from one or more of the processors, wherein the image comprises a three-dimensional topographic representation of the object surface that includes data characterizing the object surface in three dimensions superimposed with a three-dimensional light emitting representation including information describing a magnitude and three-dimensional spatial location of electro-magnetic radiation located within the object, wherein the information describing the three-dimensional spatial location characterizes the relative position in three dimensions between the three-dimensional light emitting representation and the three-dimensional topographic representation of the object surface; a graphical user interface running on one or more of the processors and providing one or more reconstruction tools, wherein when a user uses one of the reconstruction tools, the computer system reconstructs the three-dimensional light emitting representation of the electro-magnetic radiation located within the object; and
an opacity setting that allows a user to vary the transparency of the three-dimensional topographic representation of the object surface.

2. The computer system of claim 1 wherein the electro-magnetic radiation comprises a wavelength in the visible spectrum or near infrared spectrum.

3. The computer system of claim 2 wherein the electro-magnetic radiation emits luminescent or fluorescent light.

4. The computer system of claim 1 wherein when the user uses the one or more reconstruction tools, the computer system performs a tomographic reconstruction of the electro-magnetic radiation internal to the object.

5. The computer system of claim 4 wherein the one or more reconstruction tools comprise a tool that permits the user to alter a reconstruction parameter used in the tomographic reconstruction of the electro-magnetic radiation.

6. A computer system configured to display and analyze an image including three-dimensional data of an object surface and three-dimensional light data of light emitted from within the object, the computer system comprising:
one or more processors; one or more user input devices; configured to display the image and associated information in particular ways responsive to input signals from one or more of the input devices and signals from one or more of the processors, wherein the image comprises a three-dimensional topographic representation of the object surface that includes data characterizing the object surface in three dimensions superimposed with a three-dimensional light emitting representation including information describing a magnitude and three-dimensional spatial location of electro-magnetic radiation located within the object; wherein the information describing the three-dimensional spatial location characterizes the relative position in three dimensions between the three-dimensional light emitting representation and the three-dimensional topographic representation of the object surface;
a graphical user interface running on one or more of the processors and providing one or more reconstruction tools; wherein when a user uses one of the reconstruction tools, the computer system reconstructs the three-dimensional light emitting representation of the electro-magnetic radiation located within the object;
wherein the one or more reconstruction tools comprise a set of orthogonal slice tools that produce a set of slices and provide the user with electro-magnetic radiation data that intersects a plane defined by each slice.

7. The computer system of claim 1 wherein the one or more reconstruction tools comprise a select wavelengths tool that allows the user to select one or more wavelengths used in reconstructing the three-dimensional light emitting representation.

8. A computer system configured to display and analyze an image including three-dimensional data of an object surface and three-dimensional light data of light emitted from within the object, the computer system comprising:
one or more processors; one or more user input devices;
a display configured to display the image and associated information in particular ways responsive to input signals from one or more of the input devices and signals from one or more of the processors, wherein the image comprises a three-dimensional topographic representation of the object surface that includes data characterizing the object surface in three dimensions superimposed with a three-dimensional light emitting representation including information describing a magnitude and three-dimensional spatial location of electro-magnetic radiation located within the object, wherein the information describing the three-dimensional spatial location characterizes the relative position in three dimensions between the three-dimensional light emitting representation and the three-dimensional topographic representation of the object surface; and
a graphical user interface running on one or more of the processors and providing one or more reconstruction tools; wherein when a user uses one of the reconstruction tools, the computer system reconstructs the three-dimensional light emitting representation of the electro-magnetic radiation located within the object,
wherein the one or more reconstruction tools comprise a select wavelengths tool that allows the user to select one or more wavelengths used in reconstructing the three-dimensional light emitting representation; and wherein the select wavelengths tool permits the user to select a wavelength range for reconstruction of the three-dimensional light emitting representation of the electro-magnetic radiation.

9. A computer system configured to display and analyze an image including three-dimensional data of an object surface and three-dimensional light data of light emitted from within the object, the computer system comprising:
one or more processors;
one or more user input devices;
a display configured to display the image and associated information in particular ways responsive to input signals from one or more of the input devices and signals from one or more of the processors, wherein the image comprises a three-dimensional topographic representation of the object surface that includes data characterizing the object surface in three dimensions superimposed with a three-dimensional light emitting representation including information describing a magnitude and three-dimensional spatial location of electro-magnetic radiation located within the object, wherein the information describing the three-dimensional spatial location characterizes the relative position in three dimensions between the three-dimensional light emitting representation and the three-dimensional topographic representation of the object surface; and a graphical user interface running on one or more of the processors and providing one or more reconstruction tools, wherein when a user uses one of the reconstruction tools, the computer system reconstructs the three-dimensional light emitting representation of the electro-magnetic radiation located within the object, wherein the one or more reconstruction tools comprise a tissue properties tool that permits a user to select a tissue property model used in reconstructing the three-dimensional light emitting representation of the electro-magnetic radiation.

10. The computer system of claim 1 wherein the three-dimensional light emitting representation also includes a mapping of the data associated with the electro-magnetic radiation located within the object onto the three-dimensional topographic representation of the object surface.

11. The computer system of claim 1 further comprising one or more tools for defining a region of interest on the image, wherein when a user uses one of the region of interest tools, the computer system calculates information about a portion of the image for the defined region of interest.

12. The computer system of claim 11 wherein the one or more tools for defining the region of interest allow the user to graphically create at least one of a rectangle on the image, an ellipse on the image, a line on the image, and a grid on the image.

13. A computer system configured to display and analyze an image including three-dimensional data of an object surface and three-dimensional light data of light emitted from within the object, the computer system comprising:

one or more processors; one or more user input devices; a display configured to display the image and associated information in particular ways responsive to input signals from one or more of the input devices and signals from one or more of the processors, wherein the image comprises a three-dimensional topographic representation of the object surface that includes data characterizing the object surface in three dimensions superimposed with a three-dimensional light emitting representation including information describing a magnitude and three-dimensional spatial location of electro-magnetic radiation located within the object, wherein the information describing the three-dimensional spatial location characterizes the relative position in three dimensions between the three-dimensional light emitting representation and the three-dimensional topographic representation of the object surface;

a graphical user interface running on one or more of the processors and providing one or more reconstruction tools, wherein when a user uses one of the reconstruction tools, the computer system reconstructs the three-dimensional light emitting representation of the electro-magnetic radiation located within the object; and one or more tools for defining a region of interest on the image; wherein when a user uses one of the region of interest tools, the computer system calculates information about a portion of the image for the defined region of interest, wherein the one or more tools for defining the region of interest allow the user to graphically create at least one of a rectangle on the image; an ellipse on the image, a line on the image, and a grid on the image, and wherein the graphical user interface includes a line profile tool which when selected causes the computer system to open a line profile window that comprises a graph of photons or counts versus line position for a line portion corresponding to a line created on the image.

14. The computer system of claim 13 wherein the graphical user interface allows the user, via the one or more of the input devices, to move the line portion on the image or change the size of the line portion on the image.

15. A computer system configured to display and analyze an image including three-dimensional data of an object surface and three-dimensional light data of light emitted from within the object, the computer system comprising:

one or more processors; one or more user input devices; a display configured to display the image and associated information in particular ways responsive to input signals from one or more of the input devices and signals from one or more of the processors, wherein the image comprises a three-dimensional topographic representation of the object surface that includes data characterizing the object surface in three dimensions superimposed with a three-dimensional light emitting representation including information describing a magnitude and three-dimensional spatial location of electro-magnetic radiation located within the object, wherein the information describing the three-dimensional spatial location characterizes the relative position in three dimensions between the three-dimensional light emitting representation and the three-dimensional topographic representation of the object surface; and a graphical user interface running on one or more of the processors and providing one or more reconstruction tools, wherein when a user uses one of the reconstruction tools, the computer system reconstructs the three-dimensional light emitting representation of the electro-magnetic radiation located within the object;

wherein the display window includes a histogram tool which when selected causes the computer system to automatically calculate and display a statistical map of wavelength versus luminance level for the light emitting representation.

16. The computer system of claim 1 wherein the graphical user interface graphically provides a tool palette that comprises the one or more tools.

17. The computer system of claim 16 wherein the image and the tool palette are provided in separate windows.

18. The computer system of claim 17 wherein the tool palette comprises a set of thematic tool sections.

19. A computer system configured to display and analyze an image including three-dimensional data of an object surface and three dimensional light data of light emitted from within the object, the computer system comprising:

one or more processors; one or more user input devices; a display configured to display the image and associated information in particular ways responsive to input signals from one or more of the input devices and signals from one or more of the processors, wherein the image comprises a three-dimensional topographic representation of an object surface that includes data characterizing the object surface in three dimensions superimposed with a three-dimensional light emitting representation including information describing a magnitude and three-dimensional spatial location of light emitted from a surface of the three-dimensional topographic representation, wherein the information describing the three-dimensional spatial location characterizes the relative position in three dimensions between the three-dimensional light emitting representation and the three-dimensional topographic representation; and a graphical user interface running on one or more of the processors and providing one or more topographic representation tools, wherein when a user selects the one or more topographic representation tools, the computer system constructs the three-dimensional topographic representation of the object:

wherein the computer system employs one or more structured light images in building the topographic representation.

20. The computer system of claim 19 wherein the computer system outputs a pictorial representation of the three-dimensional topographic representation on the display when the user selects the one or more topographic representation tools.

21. The computer system of claim 19 wherein the topographic representation tools comprise a tool that allows the user to vary a mathematical parameter used in building the three-dimensional topographic representation.

22. A computer system configured to display and analyze an image including three-dimensional data of an object surface and three dimensional light data of light emitted from within the object, the computer system comprising:

one or more processors; one or more user input devices; a display configured to display the image and associated information in particular ways responsive to input signals from one or more of the input devices and signals from one or more of the processors, wherein the image comprises a three-dimensional topographic representation of an object surface that includes data characterizing the object surface in three dimensions superimposed with a three-dimensional light emitting representation including information describing a magnitude and three-dimensional spatial location of light emitted from a surface of the three-dimensional topographic representation, wherein the information describing the three-dimensional spatial location characterizes the relative position in three dimensions between the three-dimensional light emitting representation and the three-dimensional topographic representation; and a graphical user interface running on one or more of the processors and providing one or more topographic representation tools, wherein when a user selects the one or more topographic representation tools, the computer system constructs the three-dimensional topographic representation of the object, wherein the topographic representation tools comprise a set of orthogonal slice tools that produce a set of slices and provide a user with shape characterization of the three-dimensional topographic representation according to a plane defined by each slice.

23. The computer system of claim 22 further comprising a graphical slider tool for each slice that allows a user to control the position of each slice in the set of slices.

24. A computer system configured to display and analyze an image including three-dimensional data of an object surface and three dimensional light data of light emitted from within the object, the computer system comprising:

one or more processors; one or more user input devices; a display configured to display the image and associated information in particular ways responsive to input signals from one or more of the input devices and signals from one or more of the processors, wherein the image comprises a three-dimensional topographic representation of an object surface that includes data characterizing the object surface in three dimensions superimposed with a three-dimensional light emitting representation including information describing a magnitude and three-dimensional spatial location of a light source located within the object, wherein the information describing the three-dimensional spatial location characterizes the relative position in three dimensions between the three-dimensional light emitting representation and the three-dimensional topographic representation of the object surface; and a graphical user interface running on one or more of the processors and providing one or more spectral analysis tools, wherein when a user inputs spectral information using one of the spectral analysis tools, the computer system performs a reconstruction of the light source according to input provided with the one or more spectral analysis tools, wherein the spectral analysis tools comprise a tissue properties tool that permits the user to select a tissue property model for reconstruction of the three-dimensional light emitting representation.

25. The computer system of claim 24 wherein the spectral analysis tools comprise a select wavelengths tool that permits a user to select a wavelength for reconstruction of the three-dimensional light emitting representation.

26. A computer system configured to display and analyze an image including three-dimensional data of an object surface and three dimensional light data of light emitted from within the object, the computer system comprising:

one or more processors; one or more user input devices; a display configured to display the image and associated information in particular ways responsive to input signals from one or more of the input devices and signals from one or more of the processors, wherein the image comprises a three-dimensional topographic representation of an object surface that includes data characterizing the object surface in three dimensions superimposed with a three-dimensional light emitting representation including information describing a magnitude and three-dimensional spatial location of a light source located within the object, wherein the information describing the three-dimensional spatial location characterizes the relative position in three dimensions between the three-dimensional light emitting representation and the three-dimensional topographic representation of the object surface; and a graphical user interface running on one or more of the processors and providing one or more spectral analysis tools, wherein when a user inputs spectral information using one of the spectral analysis tools, the computer system performs a reconstruction of the light source according to input provided with the one or more spectral analysis tools, wherein the spectral analysis tools comprise a select wavelengths tool that permits a user to select a wavelength for reconstruction of the three-dimensional light emitting representation, and wherein the select wavelengths tool permits the user to select a wavelength range for reconstruction of the three-dimensional light emitting representation.

27. The computer system of claim 24 wherein the spectral analysis tools comprise a light source spectrum tool that permits the user to select a representative spectrum for the light source.

28. The computer system of claim 24 wherein the three-dimensional light emitting representation also includes a mapping of the internal light source onto the three-dimensional topographic representation of the object surface.

29. The computer system of claim 24 wherein the light source emits light that comprises a wavelength in the visible or near infrared spectrum.

30. The computer system of claim 24 wherein the spectral analysis tools comprise a plot tool which when selected by the user graphically illustrates information related to the reconstruction.

31. A computer system configured to display and analyze an image including three-dimensional light data associated with an object, the computer system comprising:
one or more processors; one or more user input devices; a display configured to display the image and associated information in particular ways responsive to input signals from one or more of the input devices and signals from one or more of the processors,
wherein the image comprises a) a first three-dimensional light emitting representation of the object, the first three-dimensional light emitting representation including first information describing a magnitude and three-dimensional spatial location of light emitted from within the object, and b) a second three-dimensional light emitting representation of the object, the second light emitting representation including second information describing the magnitude and three-dimensional spatial location of light emitted from within the object, wherein the first information and second information characterize the relative position in three dimensions between the first three-dimensional light emitting representation and the second three-dimensional light emitting representation;
a graphical user interface running on one or more of the processors and providing one or more evaluation tools, wherein when a user uses one of the reconstruction tools, the computer system quantitatively evaluates the first information relative to the second information and a tool that allows the user to create an overlay image for a result of the quantitative evaluation.

32. The computer system of claim 31 wherein the quantitative evaluation comprises performing a mathematical operation on the first information and the second information.

33. A computer system configured to display and analyze an image including three-dimensional light data associated with an object, the computer system comprising: one or more processors; one or more user input devices; a display configured to display the image and associated information in particular ways responsive to input signals from one or more of the input devices and signals from one or more of the processors, wherein the image comprises a) a first three-dimensional light emitting representation of the object, the first three-dimensional light emitting representation including first information describing a magnitude and three-dimensional spatial location of light emitted from within the object, and b) a second three-dimensional light emitting representation of the object, the second light emitting representation including second information describing the magnitude and three-dimensional spatial location of light emitted from within the object, wherein the first information and second information characterize the relative position in three dimensions between the first three-dimensional light emitting representation and the second three-dimensional light emitting representation; and
a graphical user interface running on one or more of the processors and providing one or more evaluation tools, wherein when a user uses one of the reconstruction tools, the computer system quantitatively evaluates the first information relative to the second information,
wherein the quantitative evaluation comprises performing a mathematical operation on the first information and the second information, and wherein the tool allows the user to subtract the first information from the second information.

34. The computer system of claim 33 wherein the first information includes tissue autofluorescence information and the second three-dimensional light emitting representation includes a fluorescent image.

35. A computer system configured to display and analyze an image including three-dimensional light data associated with an object, the computer system comprising: one or more processors; one or more user input devices; a configured to display the image and associated information in particular ways responsive to input signals from one or more of the input devices and signals from one or more of the processors, wherein the image comprises a) a first three-dimensional light emitting representation of the object, the first three-dimensional light emitting representation including first information describing a magnitude and three-dimensional spatial location of light emitted from within the object, and b) a second three-dimensional light emitting representation of the object, the second light emitting representation including second information describing the magnitude and three-dimensional spatial location of light emitted from within the object,
wherein the first information and second information characterize the relative position in three dimensions between the first three-dimensional light emitting representation and the second three-dimensional light emitting representation;
a graphical user interface running on one or more of the processors and providing one or more evaluation tools, wherein when a user uses one of the reconstruction tools, the computer system quantitatively evaluates the first information relative to the second information and a tool that allows the user to select the first three-dimensional light emitting representation from a list of three-dimensional light emitting representations.

36. The computer system of claim 31 wherein the first three-dimensional light emitting representation and the second three-dimensional light emitting representation are displayed in the same window.

37. A computer system configured to display and analyze an image including three-dimensional light data associated with an object, the computer system comprising: one or more processors; one or more user input devices; a display configured to display the image and associated information in particular ways responsive to input signals from one or more of the input devices and signals from one or more of the processors, wherein the image comprises a) a first three-dimensional light emitting representation of the object, the first three-dimensional light emitting representation including first information describing a magnitude and three-dimensional spatial location of light emitted from within the object, and b) a second three-dimensional light emitting representation of the object, the second light emitting representation including second information describing the magnitude and three-dimensional spatial location of light emitted from within the object, wherein the first information and second information characterize the relative position in three dimensions between the first three- dimensional light emitting representation and the second three-dimensional light emitting representation; and a graphical user interface running on one or more of the processors and providing one or more evaluation tools, wherein when a user uses one of the reconstruction tools, the computer system quantitatively evaluates the first information relative to the second information, wherein the tool allows the user to: add the first information and the second information, multiply the first information and the second information, divide the first information by the second information or divide the second information by the first information.

\* \* \* \* \*

UNITED STATES PATENT AND TRADEMARK OFFICE
CERTIFICATE OF CORRECTION

PATENT NO. : 7,581,191 B2 Page 1 of 1
APPLICATION NO. : 11/006294
DATED : August 25, 2009
INVENTOR(S) : Rice et al.

It is certified that error appears in the above-identified patent and that said Letters Patent is hereby corrected as shown below:

On the Title Page of the Patent:

Item (*) Notice delete "781 days" insert --1209 days--.

Item (75) Inventors:   Change the third inventor's name from "Binoy Mirvar" to --Binoy Marvar--.

In the Specification:

Col. 20, line 41, change "ails" to --arts--.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

PATENT NO.       : 7,581,191 B2                                      Page 1 of 1
APPLICATION NO.  : 11/006294
DATED            : August 25, 2009
INVENTOR(S)      : Rice et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1209 days.

Signed and Sealed this

Fourteenth Day of September, 2010

David J. Kappos
*Director of the United States Patent and Trademark Office*